(12) United States Patent
Marrs et al.

(10) Patent No.: US 6,562,023 B1
(45) Date of Patent: May 13, 2003

(54) CATHETER CONNECTOR INCLUDING SEAL RING AND METHOD

(75) Inventors: James C. Marrs, Minneapolis, MN (US); Chad Qinsheng Cai, Woodbury, MN (US); William L. Beling, New Brighton, MN (US); Harry A. Puryear, Shoreview, MN (US)

(73) Assignee: Deltec Inc., St. Paul, MN (US)

( * ) Notice: Subject to any disclaimer, the term of this patent is extended or adjusted under 35 U.S.C. 154(b) by 0 days.

(21) Appl. No.: 09/673,709

(22) PCT Filed: Apr. 23, 1999

(86) PCT No.: PCT/US99/08507
§ 371 (c)(1),
(2), (4) Date: Jan. 16, 2001

(87) PCT Pub. No.: WO99/53981
PCT Pub. Date: Oct. 28, 1999

(51) Int. Cl.[7] .................. A61M 25/16; A61M 25/18; A61M 39/00; A61M 39/10; A61M 31/00
(52) U.S. Cl. .................. 604/533; 604/534; 604/535; 604/536; 604/537; 604/538; 604/539; 604/288.01; 604/288.04
(58) Field of Search ................. 285/371; 604/93.01, 604/175, 533–539, 288.04, 288.01

(56) References Cited

U.S. PATENT DOCUMENTS

| | | | | |
|---|---|---|---|---|
| 5,127,626 A | * | 7/1992 | Hilal et al. | 251/149 |
| 5,147,305 A | * | 9/1992 | Nakamura et al. | 604/110 |
| 5,171,216 A | * | 12/1992 | Dasse et al. | 604/43 |
| 5,185,003 A | | 2/1993 | Brethauer | |
| 5,279,597 A | * | 1/1994 | Dassa et al. | 604/283 |
| 5,558,641 A | | 9/1996 | Glantz et al. | |
| 5,562,618 A | * | 10/1996 | Cai et al. | 604/93 |
| 6,019,748 A | * | 2/2000 | Lopez | 604/249 |

* cited by examiner

Primary Examiner—Gregory Huson
Assistant Examiner—Anuradha Ramana
(74) Attorney, Agent, or Firm—Merchant & Gould P.C.

(57) ABSTRACT

A catheter connector includes an outlet tube (34, 36), and a compression seal (140) defining an undulating shape to product ring seals during use. A cam slot formed on a lever arm is useable in locking a locking sleeve (120) of the connector. The lever arm acts as a compensating mechanism for over compression of the seal. The catheter tip (32a) is received in a tip recess (92) of the connector. The connector is useable on an implanted port (20), including a dual port with parallel outlet tubes (34, 36), and a dual lumen catheter (24).

11 Claims, 22 Drawing Sheets

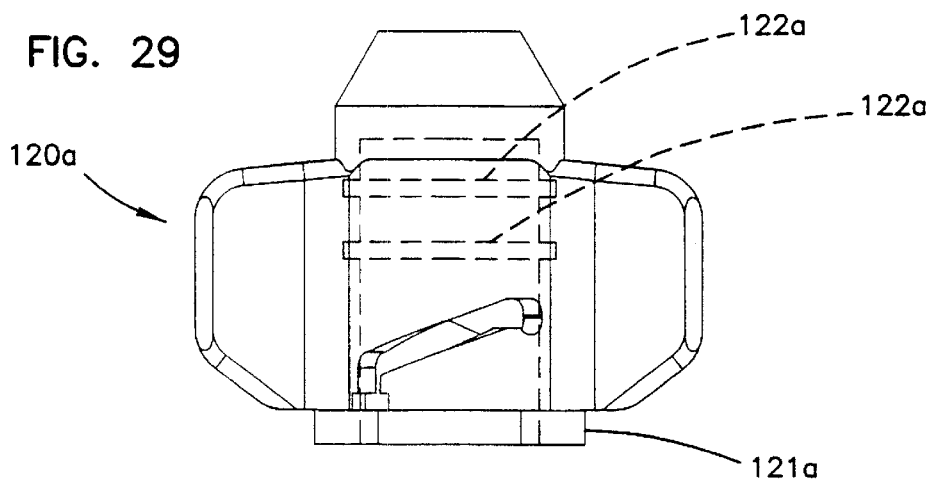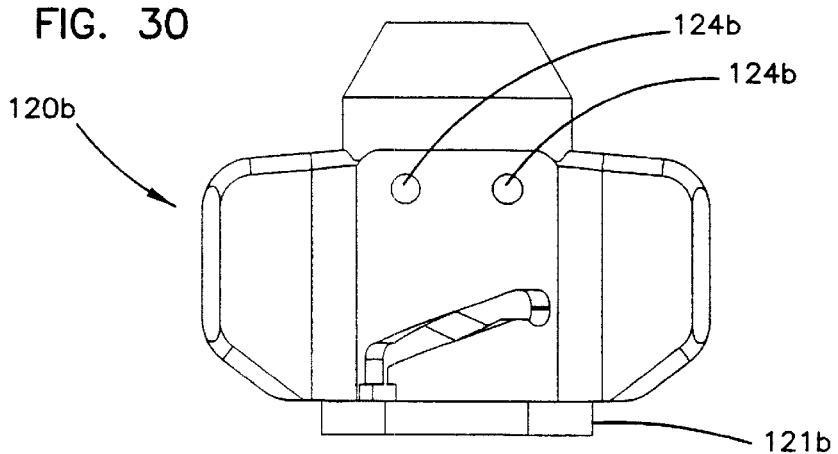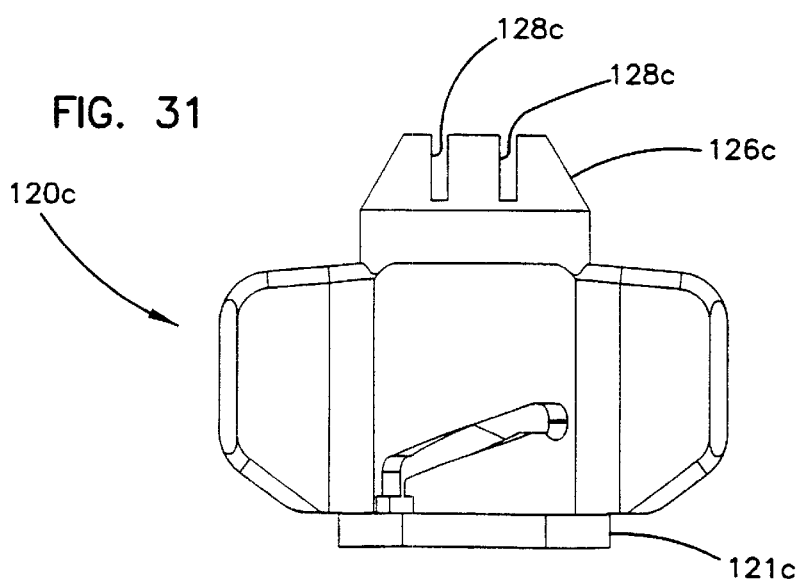

CATHETER CONNECTOR INCLUDING SEAL RING AND METHOD

This application is a 371 of PCT/US99/08507 filed April 23, 1999 which claims the benefit of U.S. Provisional Application No. 60/126,419 filed April 23, 1998.

FIELD OF THE INVENTION

This invention relates to catheter connectors and methods for connection generally, and more specifically to catheter connectors and methods for portal assemblies.

BACKGROUND OF THE INVENTION

The treatment of certain diseases of the human body or an animal's body often requires infusion of drugs, blood products, nutritional fluids, or other fluids into the patient's venous or arterial system, the patient's peritoneal or epidural space, or other locations within the patient's body. One system which is useful when repeated access for infusion is needed utilizes an implanted portal assembly which is accessed percutaneously to infuse the fluid to the desired location. A similar arrangement can be used to draw blood from an artery or vein for blood sampling purposes, or to draw other body fluids.

Such an implanted assembly includes a port which is implanted under the skin and attached to the chest wall or other convenient body location. The port includes a septum for accessing an interior of the port. The septum is located directly under the skin and is penetrable by a needle. Drugs or other fluids can be introduced into the port (or fluids withdrawn from the port) by percutaneously inserting the needle through the septum of the port. The port includes an outlet member which is connected via connection structure to one end of a flexible elastic catheter which leads to the infusion (or withdrawal) site in the patient's body.

U.S. Pat. No. 4,880,414 issued Nov. 14, 1989, and U.S. Pat. No. 4,723,948 issued Feb. 9, 1988 are two examples of different connection structure for connecting a catheter to a port.

Such an implantable port device of this type may remain in the patient's body for a long period of time, such as several months. A significant concern is that the connection between the catheter and the port remain secure and fluid tight during the period of implantation. The catheter and port may be subjected to various external forces acting to separate the catheter from the port. Should the connection fail, the fluids injected into the port would not be transported to the targeted infusion site and instead the fluid would be dispensed at the site of the port. This can be a particular concern in the case of certain drug therapies, such as chemotherapy, in which the drugs are highly concentrated and dangerous if misdirected in the patient's body. Withdrawal of fluids would also be adversely affected if the connection failed.

A further concern is the ease and reliability in which the port can be connected to the catheter. Typically, the connection between the port and the catheter is made during the implantation surgery when the portal assembly is first installed. A surgeon handling the implantation surgery will be wearing gloves, and the gloves or port may be covered with body fluids from the surgery. There is a need for the connector structure to be easy to use in these circumstances and to do so reliably. There is also a need for the connection to be made quickly to keep the length of the surgery as short as possible.

Another concern with respect to implantable devices of this type is that it may be necessary to disconnect the catheter from the port after implantation if the catheter or port needs to be changed. One concern is whether the connection between the catheter and port is easily disconnectable.

A further concern is the size of the catheter connector. A connector that is too bulky can be a problem for the patient. Intricate parts can be a problem for manufacture of the connector, and also use of the connector, especially if the parts are small in size.

U.S. Pat. No. 5,562,618 issued Oct. 8, 1996 is a further example of connection structure for connecting a catheter to a port. Specifically, the '618 patent shows a connector 26 for use in connecting a dual lumen catheter 24 to a port having two different needle access sites 48 and two outlet tubes 34, 36. A sleeve 102 and a lock ring 120 connect catheter 24 to outlet tubes 34, 36. Connector 26 of the '618 patent bunches up an end of catheter 24 during use as shown in FIG. 6.

There continues to be a need in the art for catheter connectors and connection methods generally, and more specifically catheter connectors and methods for connecting catheters to ports which address at least some of the above concerns and other concerns in the art. There is a particular need for connectors and methods for sealing a multi-lumen catheter having at least two lumens to multiple outlet tubes.

BRIEF DESCRIPTION OF THE DRAWINGS

In the drawings, where like numerals refer to like features throughout the several views:

FIG. 29 is a top view of a first alternative locking sleeve.

FIG. 30 is a top view of a second alternative locking sleeve.

FIG. 31 is a top view of a third alternative locking sleeve.

SUMMARY OF THE INVENTION

Figure 1:
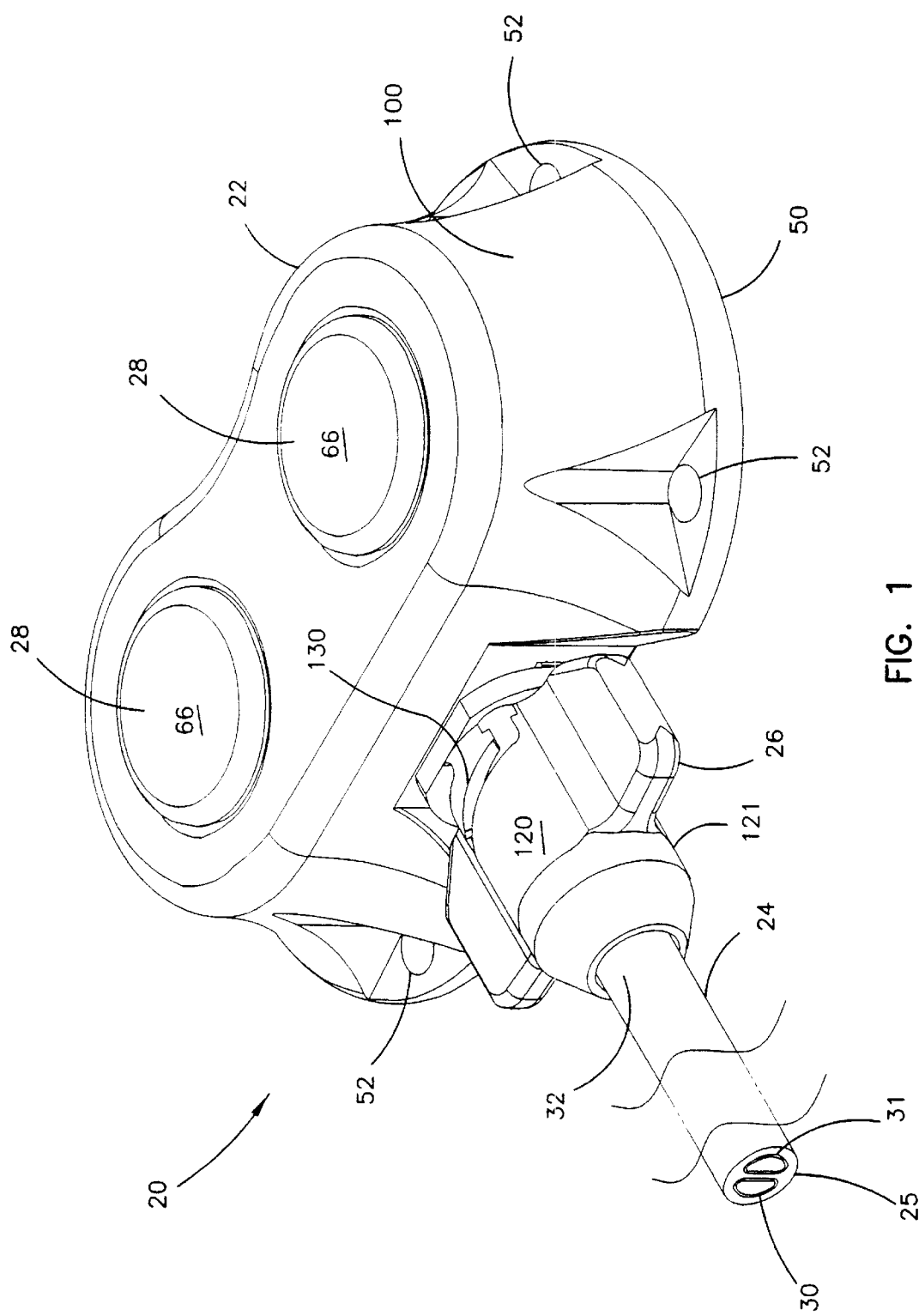
FIG. 1 is a perspective view of a portal assembly according to the present invention including a catheter connector.

One aspect of the present invention relates to a catheter connector including a compression fitting for sealing a catheter to a tube of a base arrangement, such as a port. The base arrangement includes a stop surface. The connector includes a locking member including a stop surface. The two stop surfaces compress a compression seal to seal the catheter to the tube. The locking member mounts to the base arrangement with a cam and bayonet system. The cam is formed on a moveable lever arm which functions as a compensating member. The locking member is preferably a sleeve which holds the compression seal in an internal chamber. The compensating member is provided to allow for consistent sealing of the catheter. Other compensating members which can be provided in combination with the lever arm or instead of the lever arm include recesses or holes in the locking sleeve to receive portions of the compression seal, and/or a flexible stop surface within the locking sleeve.

Another aspect of the present invention also relates to a compression fitting where the compression seal which seals the catheter to the tube or tubes has an undulating shape for forming a plurality of ring seals.

A further aspect of the present invention also relates to a compression fitting where the tip of the catheter is received in a generally cylindrical recess of the base arrangement. The recess includes a stop surface for engaging the end of the catheter. Preferably, an inspection hole is provided for visually checking whether the catheter is fully inserted into the recess.

Preferred base arrangements in accordance with the invention include implantable ports including at least one pierceable septum. Preferred base arrangements also include two outlet tubes which are sealed to a dual lumen catheter by the compression fitting. The preferred outlet tubes and lumens of the dual port and catheter includes rounded D-shapes with curved corners.

The present invention also relates to methods of use of a catheter connector where the connector includes a compression fitting including a compression seal. One aspect of the method of use in accordance with the present invention relates to providing a cam slot and bayonet to lock the compression fitting, where the method includes positioning the cam slot on a moveable lever arm, and moving the lever arm during locking of the compression fitting to compensate for overcompression of the seal. Further methods include moving an end portion of the locking sleeve to compensate for overcompression of the seal. Still further methods include flowing the seal into a recess or hole of the locking sleeve for overcompression of the seal.

Another aspect of the method of use in accordance with the present invention relates to forming a plurality of ring seals with the compression seal between the catheter and the outlet tube or tubes of the connector. A further aspect of the method of use in accordance with the present invention relates to positioning the end of the catheter within the connector in a generally cylindrical recess, the end of the catheter positioned within the recess and over the outlet tube or tubes so as to engage a stop surface.

DETAILED DESCRIPTION OF THE PREFERRED EMBODIMENTS

The present invention provides a connector for connecting a catheter to a base arrangement with at least one outlet tube. The base arrangement preferably includes an access port for implantation under the skin and two side by side outlet tubes. The connector includes a locking member and a compression seal which cooperates with the base arrangement to radially inwardly compress the catheter to the outlet tube or tubes. The preferred compression seal produces a plurality of ring seals between the catheter and the outlet tube or tubes. A cam and bayonet arrangement with an overcenter portion locks the locking member to the base arrangement and provides consistent sealing of the catheter, as well as a mechanical advantage for the operator, and secure locking. The connector includes a compensating feature for allowing consistent locking of the locking member to the base arrangement. The base arrangement also receives an end of the catheter for further sealing of the catheter to the base arrangement.

Referring now to FIGS. 1 through 8A, a portal assembly 20 is shown. FIGS. 9 through 28 show features of portal assembly 20 in greater detail. Portal assembly 20 includes a portal or port 22, a catheter 24, and a connector 26 connecting catheter 24 to port 22 with a fluid-tight seal. Portal assembly 20 is implantable under the skin for use in infusing drugs or other fluids to the patient entering at port 22 and exiting at a distal end 25 of catheter 24. Portal assembly 20 is also utilized in some situations as a port for withdrawing blood or other fluids from the body via catheter 24. In either case, catheter 24 has distal end 25 at the desired location within the patient's body. Connector 26 connects a proximate end 32 of catheter 24 to port 22. Connector 26 also permits disconnection of catheter 24 from port 22 at the desired time. Catheter 24 is made from a bio-compatible and flexible, elastic polymeric material, such as silicone or polyurethane.

Figure 2:
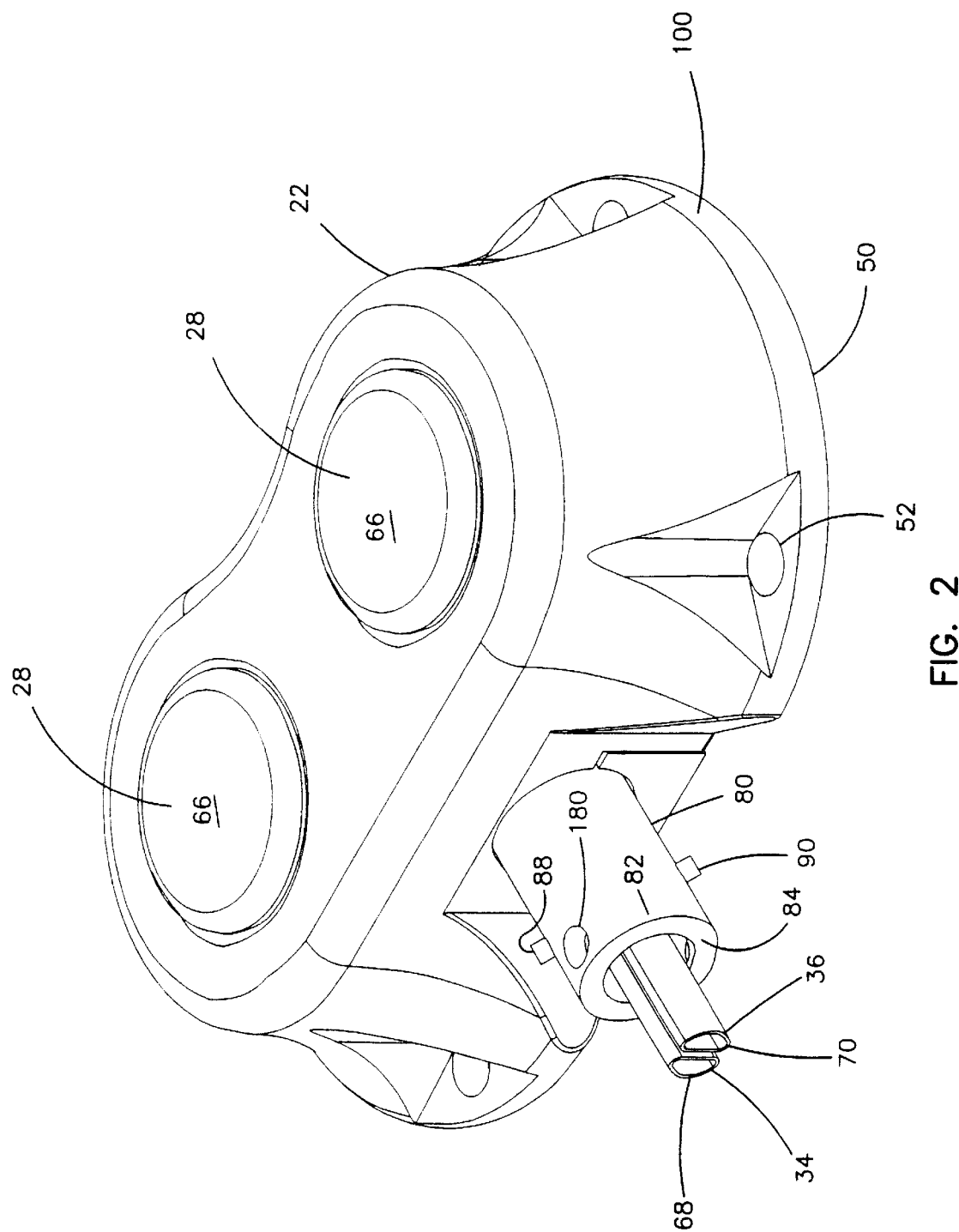
FIG. 2 is a perspective view of the port of FIG. 1.
Figure 3:
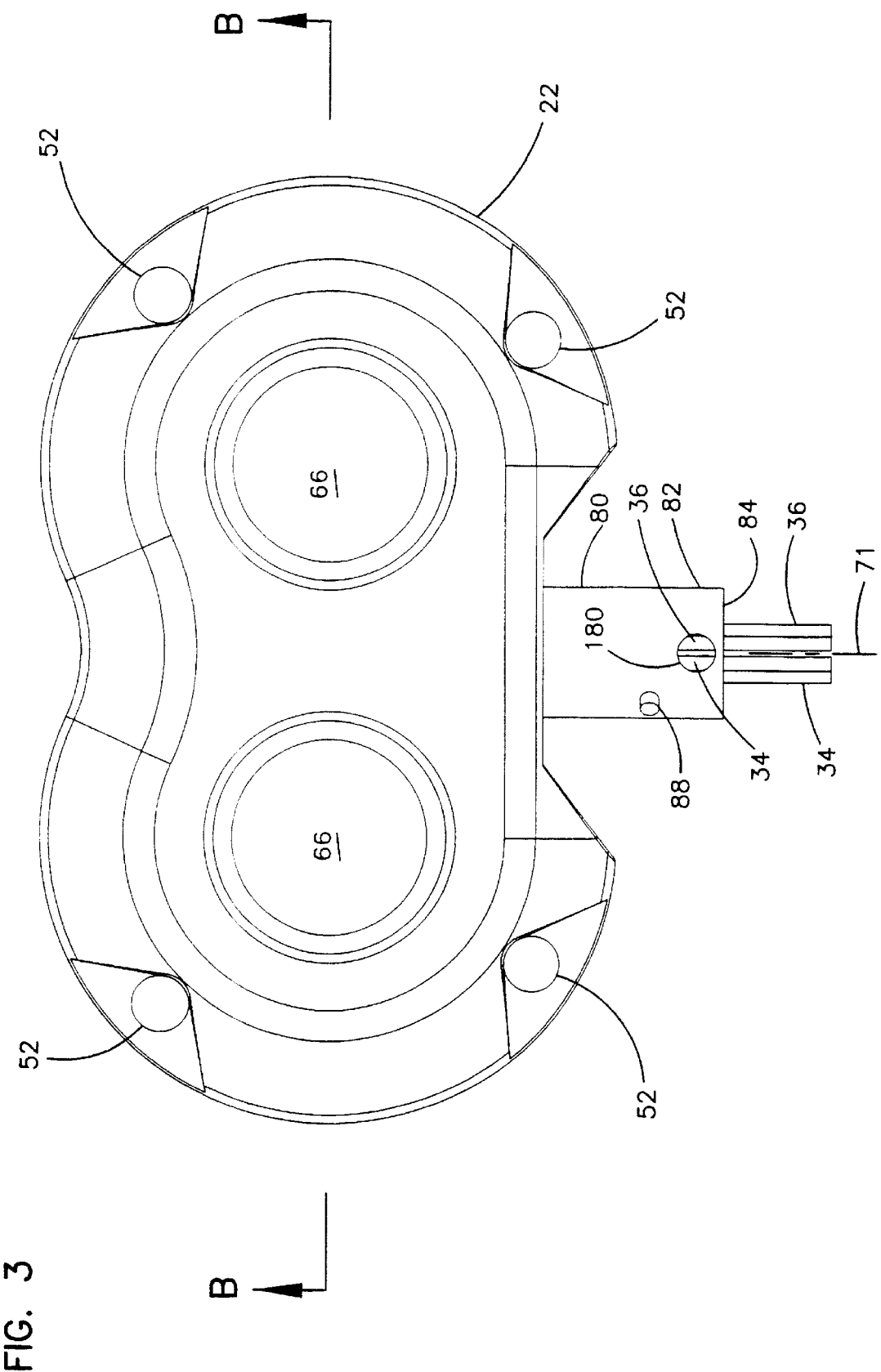
FIG. 3 is a top view of the port.
Figure 4:
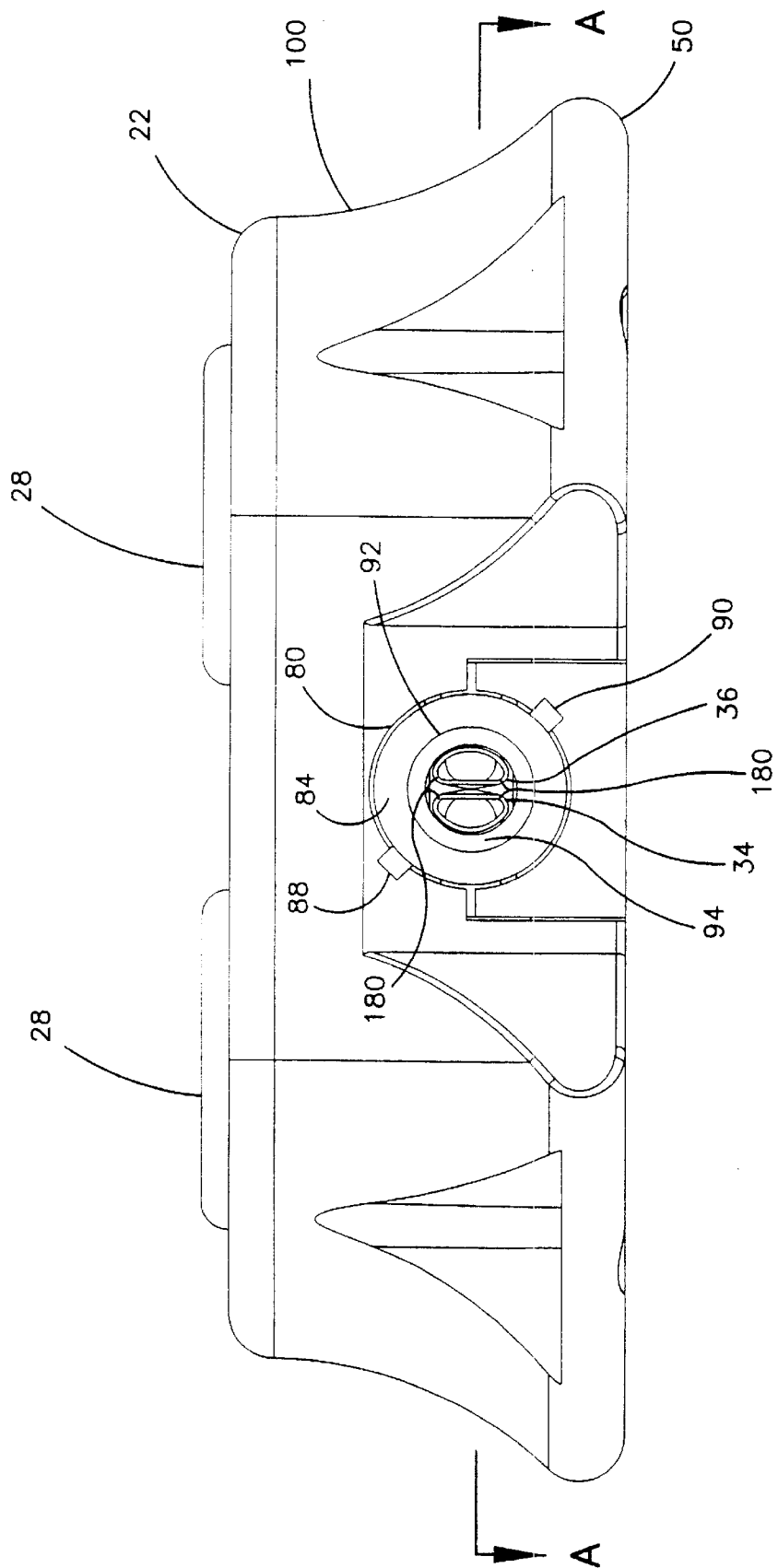
FIG. 4 is a front view of the port.
Figure 5:
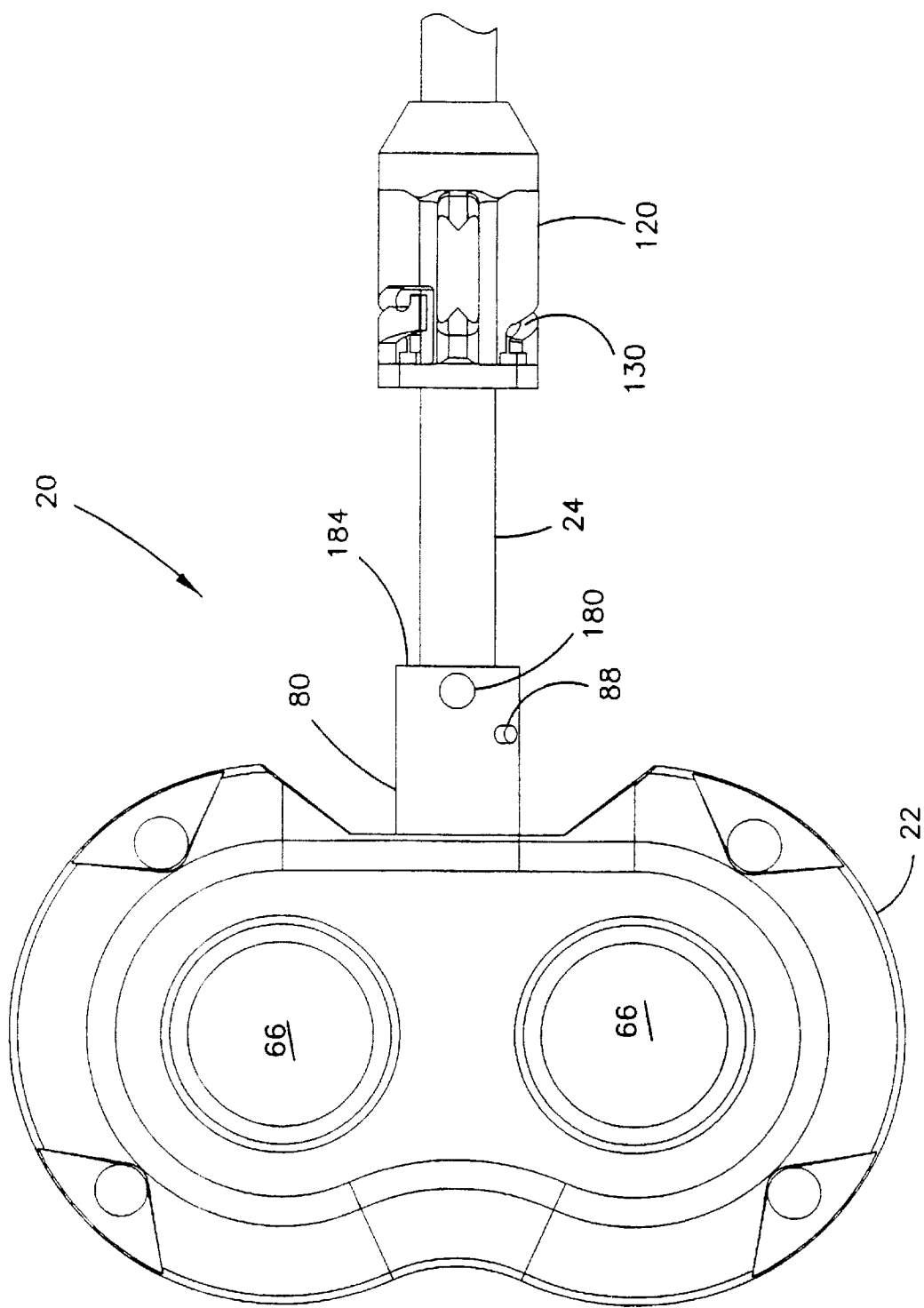
FIG. 5 is a top view of the port, showing the catheter positioned on the outlet tubes, and the locking sleeve positioned over the catheter ready to connect the catheter to the port.
Figure 6:
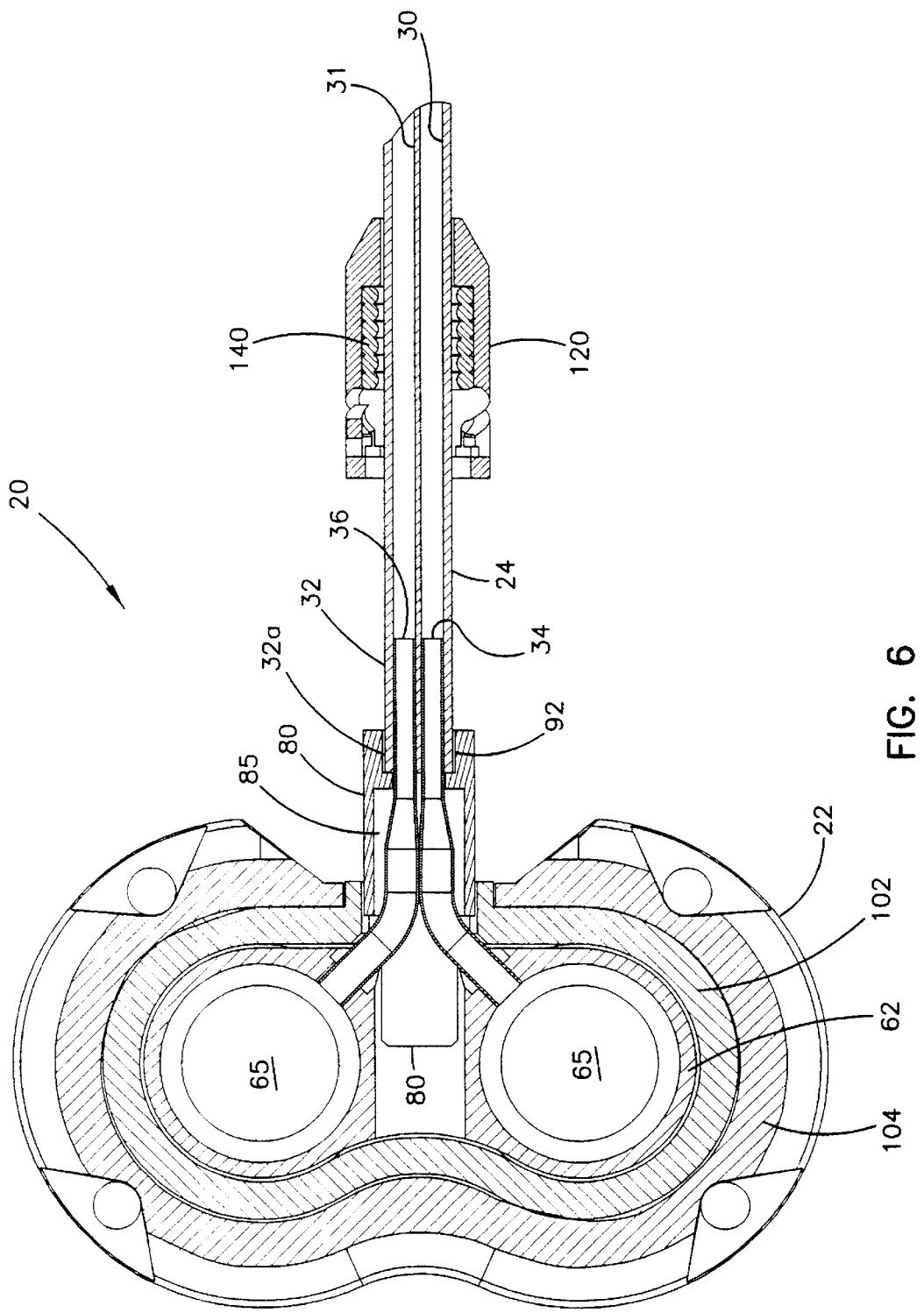
FIG. 6 is a cross-sectional top view of FIG. 5, taken along lines A—A of FIG. 4.
Figure 28:
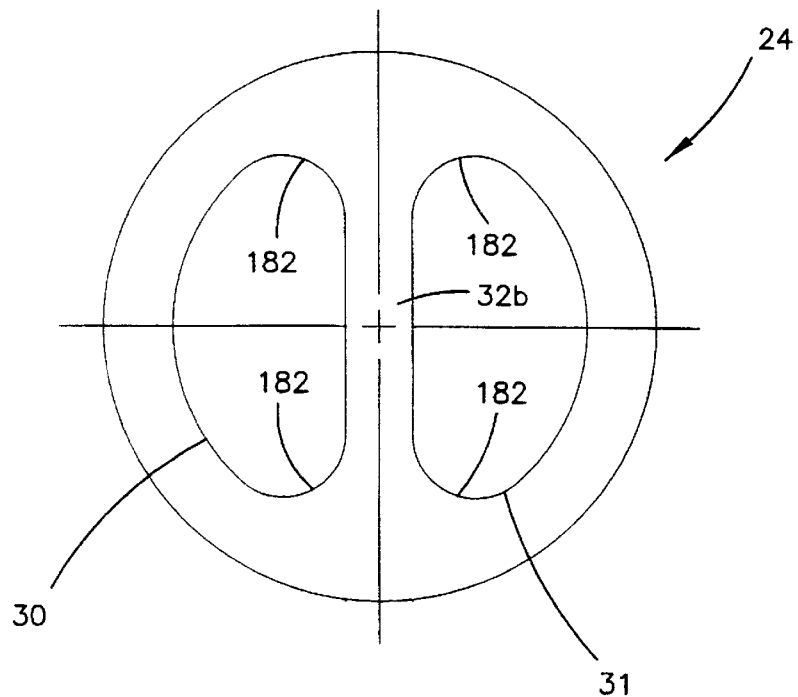
FIG. 28 is an end view of the dual lumen catheter.

In the embodiment shown, port 22 is a dual port. Two different needle access sites 28 are provided with a dual port configuration. As will be described below, the dual port configuration includes two outlet tubes 34, 36 as shown in FIG. 2. For example, catheter 24 is a dual lumen configuration with a first lumen 30 and a second lumen 31 as shown in FIGS. 1, 6 and 28. Distal ends 68, 70 of outlet tubes 34, 36 extend generally parallel to axis 71 and in close proximity to one another. Each lumen 30, 31 of catheter 24 is in fluid communication with one of outlet tubes 34, 36. Additional outlet tubes and an appropriately configured catheter 24 can be provided if more than two access sites are provided.

It is to be appreciated that portal assembly 20 can instead be a single port configuration, with a single outlet tube, and catheter 24 can be a single lumen. It is to be appreciated that, for a multi-port configuration, outlet tubes 34, 36 can be positioned in a spaced apart configuration (not shown). In that case, a connector 26 would be provided for each outlet tube and catheter 24 would be a single lumen.

Figure 14:
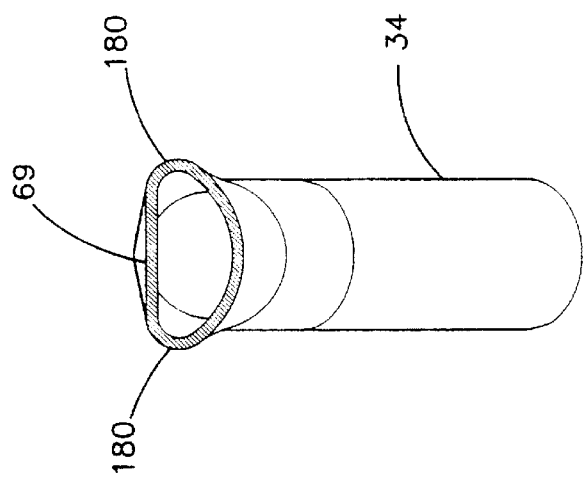
FIG. 14 is a cross-sectional end view of the outlet tube of FIG. 13 taken along lines C—C.
Figure 13:
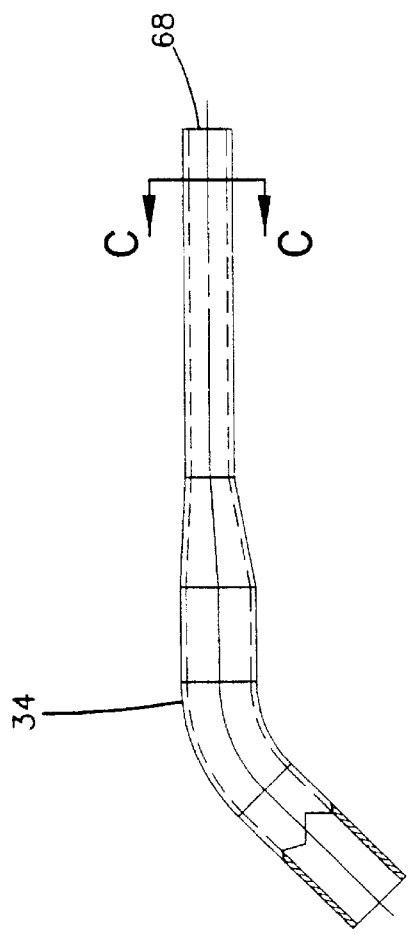
FIG. 13 is a top view of one of the outlet tubes with a proximal end portion shown in cross-section.
Figure 15:
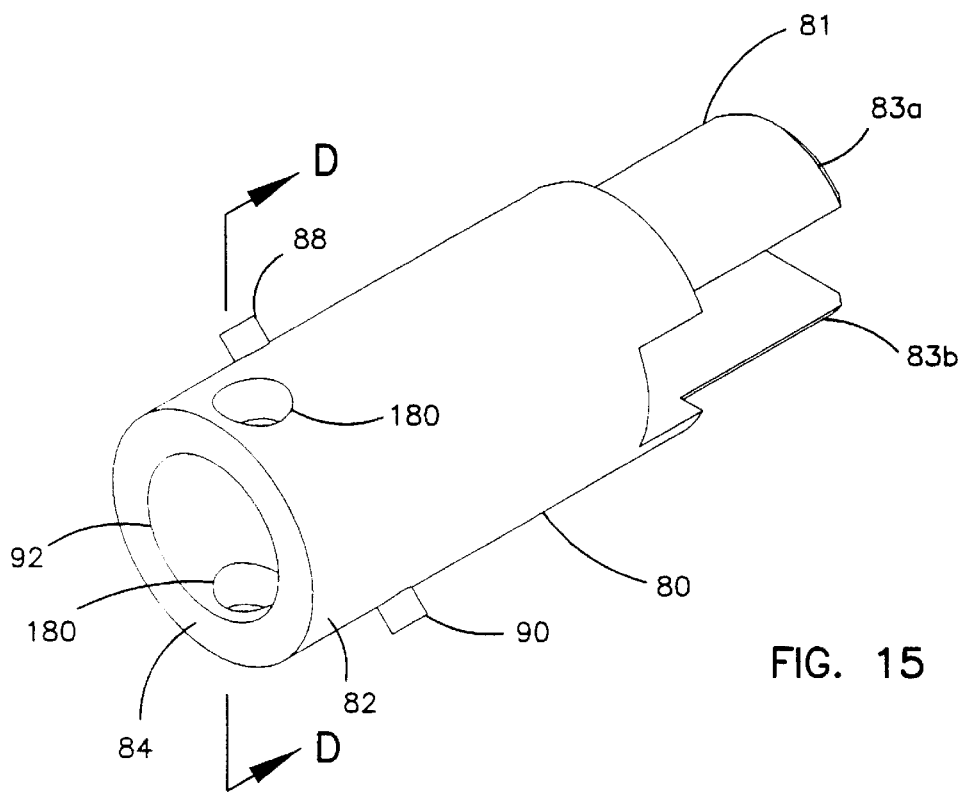
FIG. 15 is a perspective view of the outlet tube support.
Figure 16:
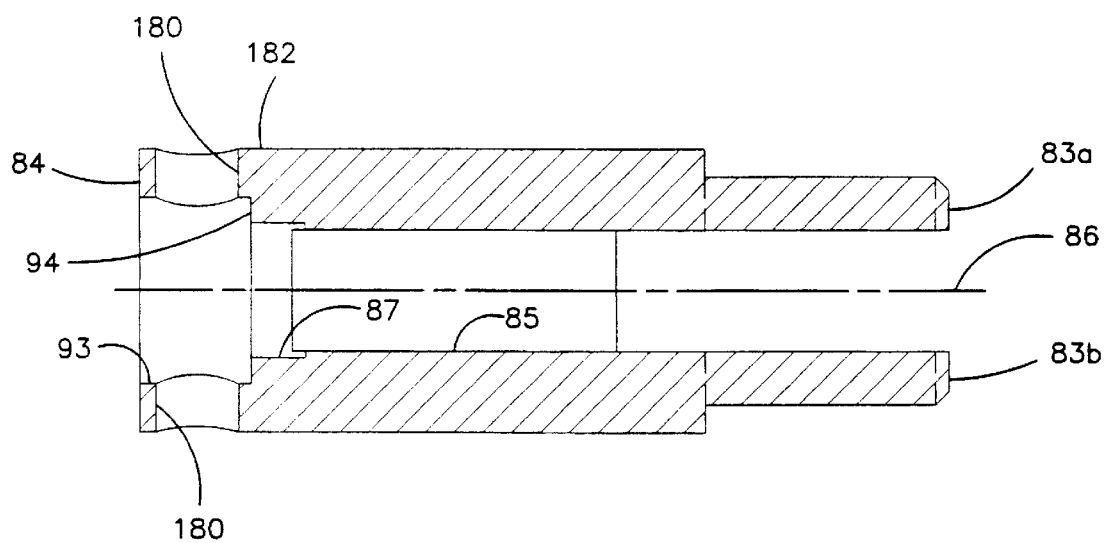
FIG. 16 is a cross-sectional side view of the outlet tube support taken along lines D—D of FIG. 15.
Figure 17:
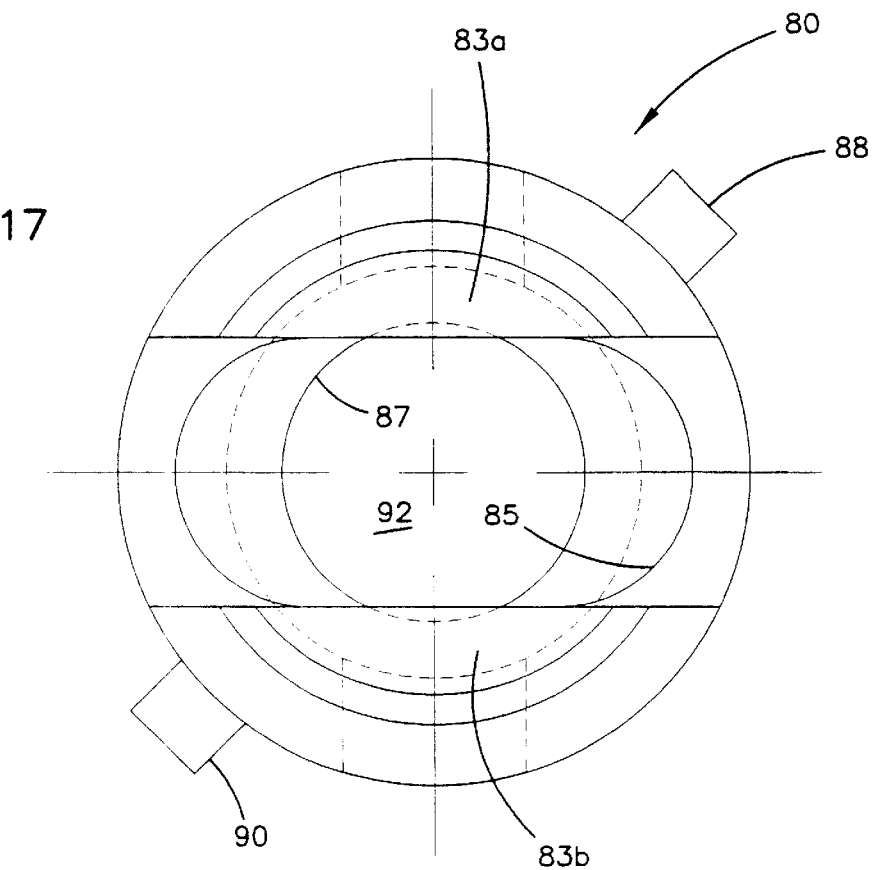
FIG. 17 is a rear end view of the outlet tube support.
Figure 18:
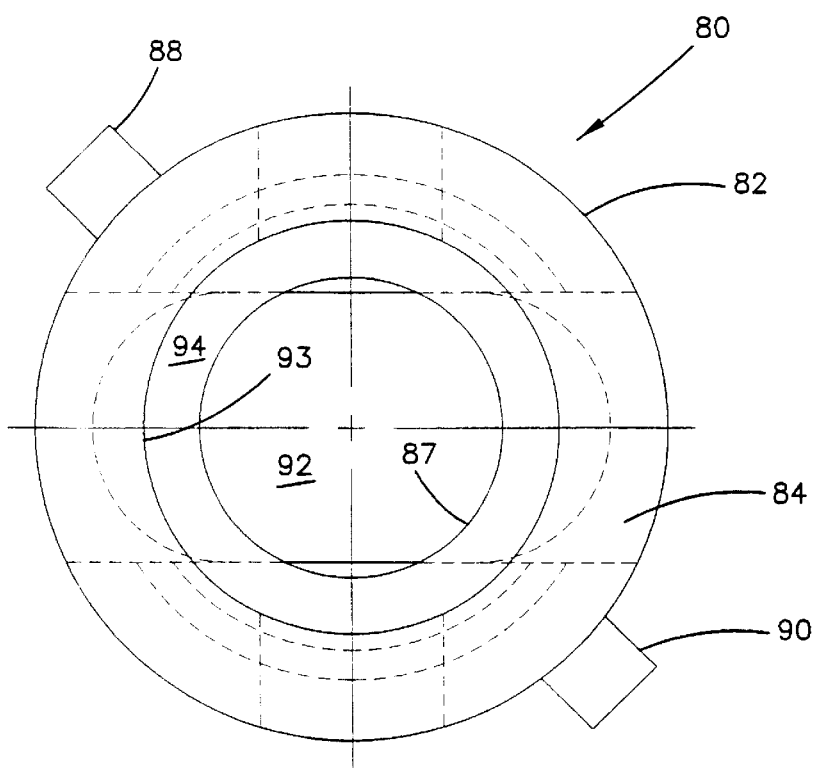
FIG. 18 is a front end view of the outlet tube support.
Figure 19:
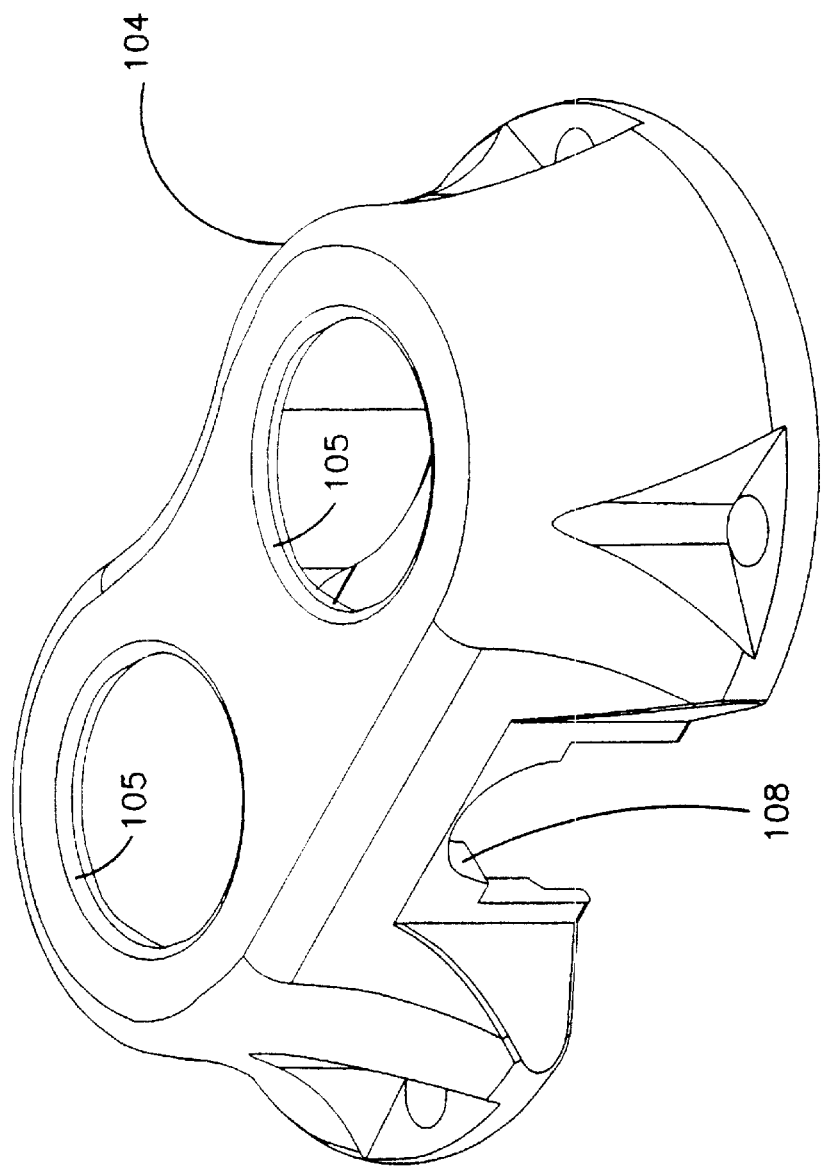
FIG. 19 is a perspective view of the cowl of the outer housing of the port.
Figure 20:
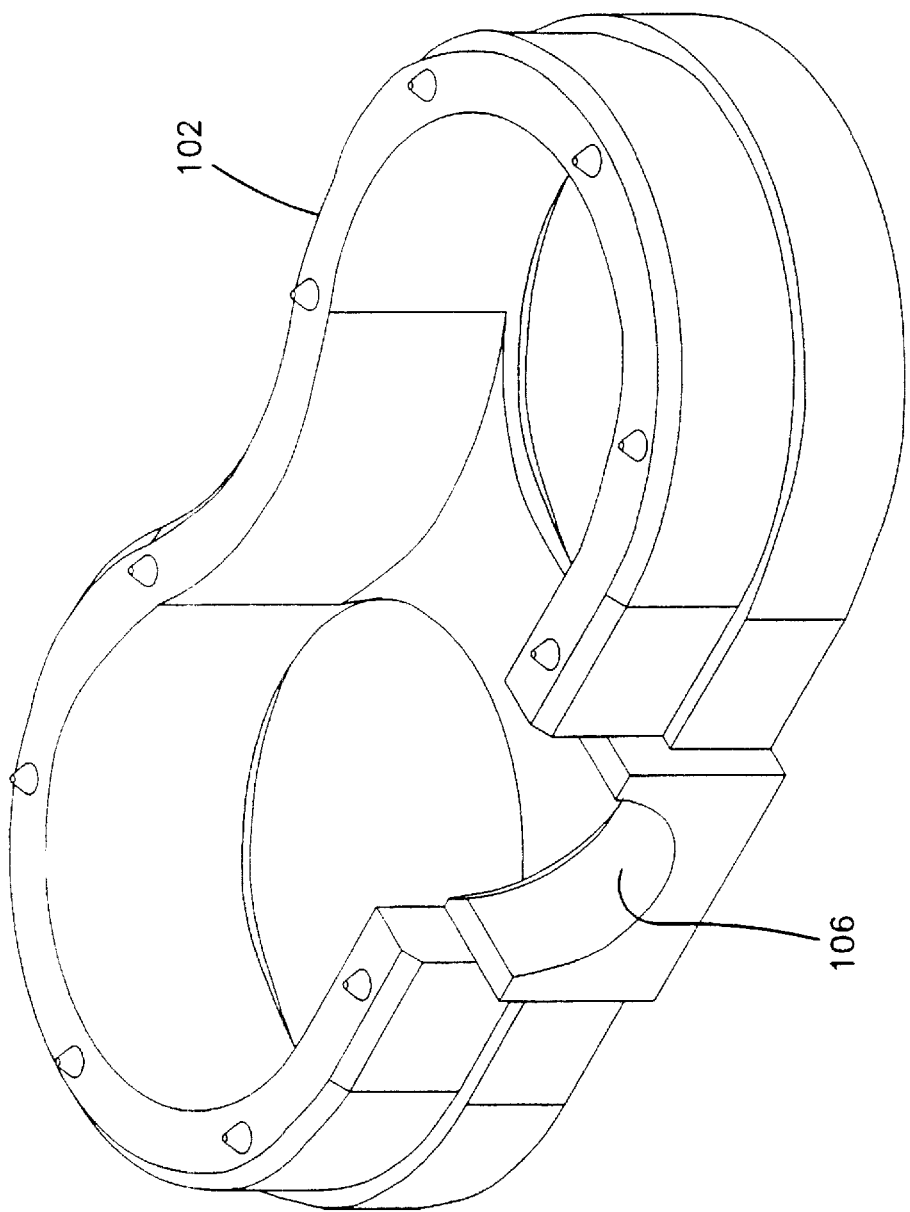
FIG. 20 is a perspective view of the base of the outer housing of the port.
Figure 21:
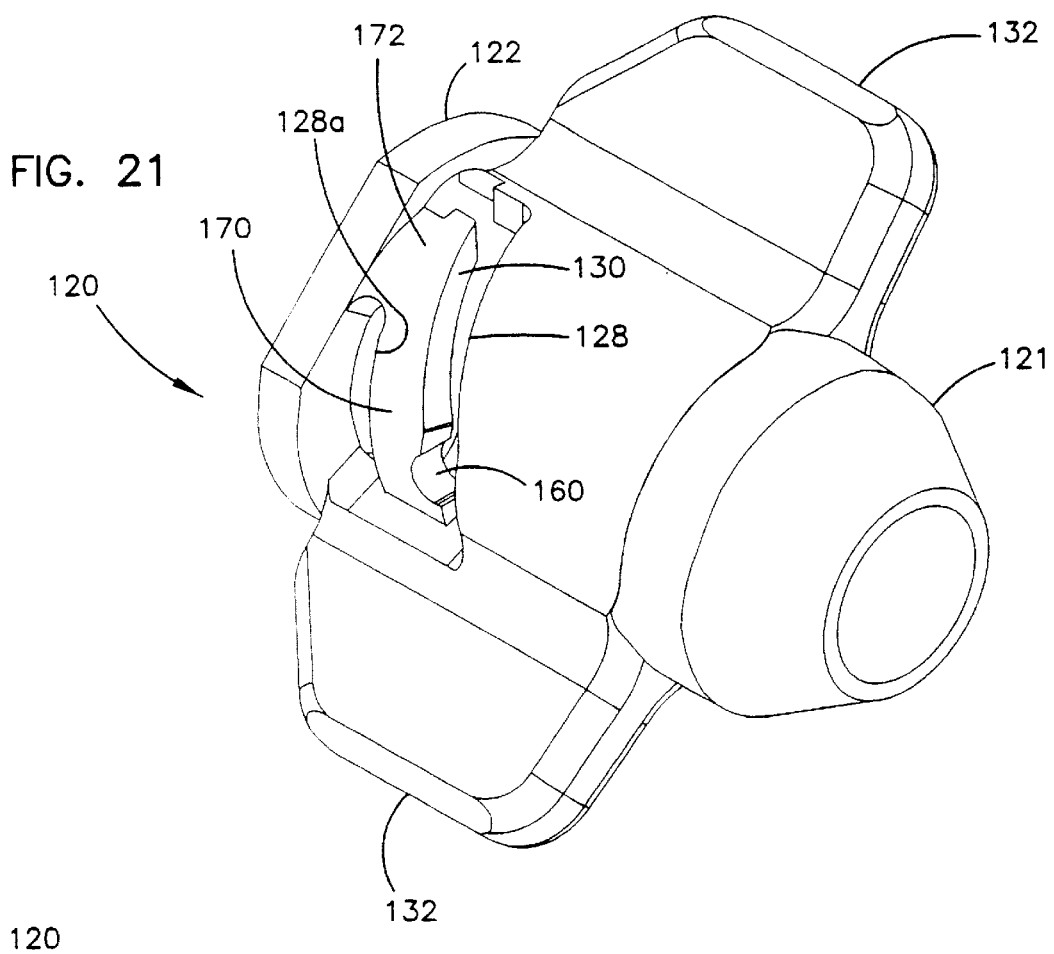
FIG. 21 is a perspective view of the locking sleeve.
Figure 24:
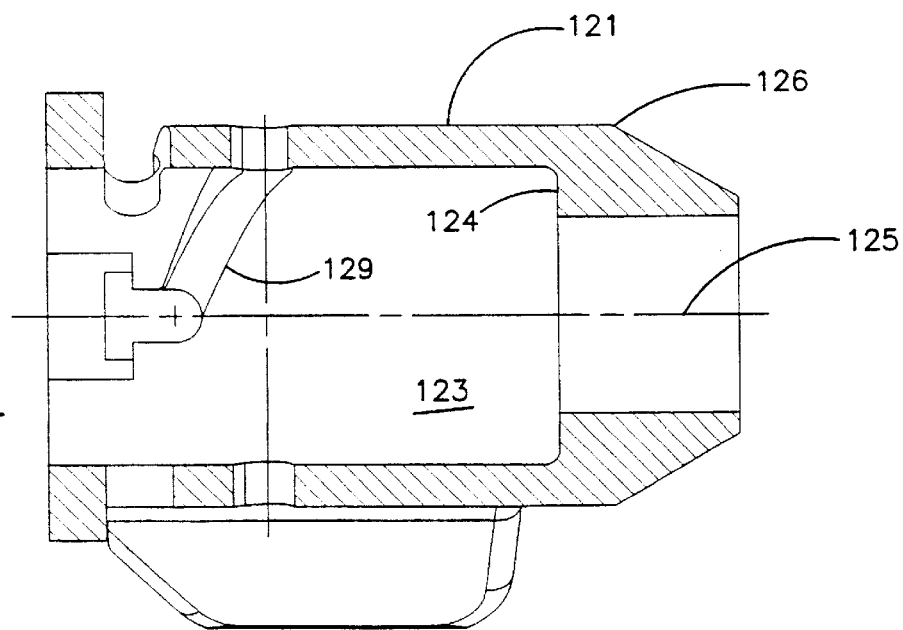
FIG. 24 is a cross-sectional view of the locking sleeve taken along lines E—E of FIG. 23.
Figure 22:
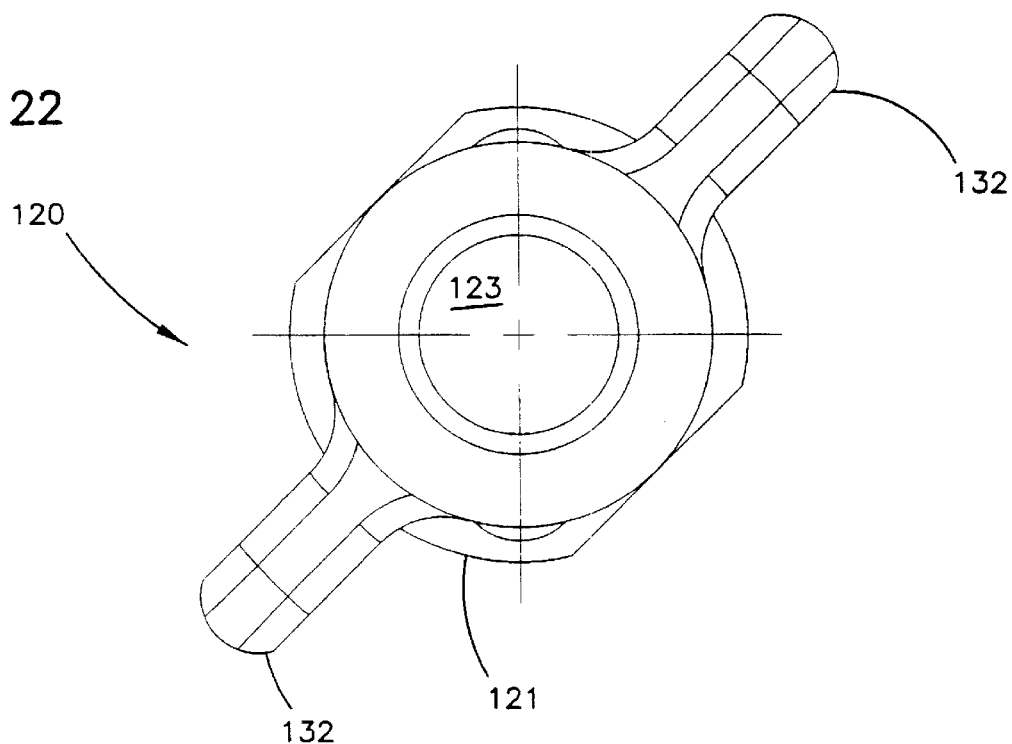
FIG. 22 is an end view of the locking sleeve.
Figure 23:
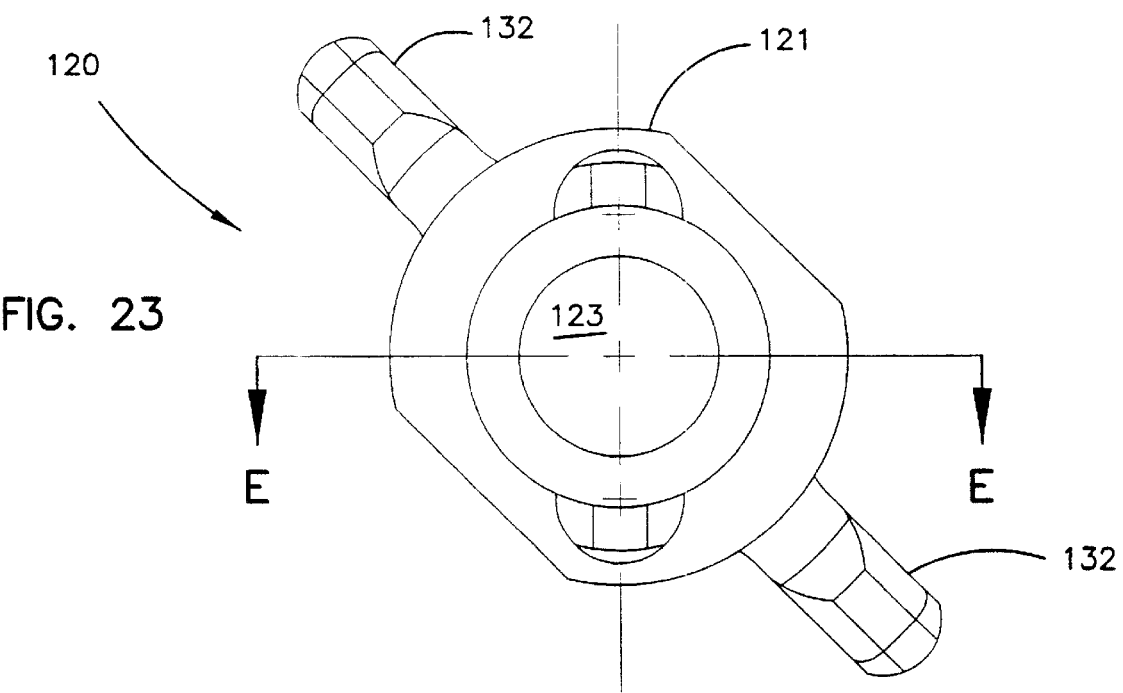
FIG. 23 is an opposite end view of the locking sleeve relative to FIG. 22.
Figure 25:
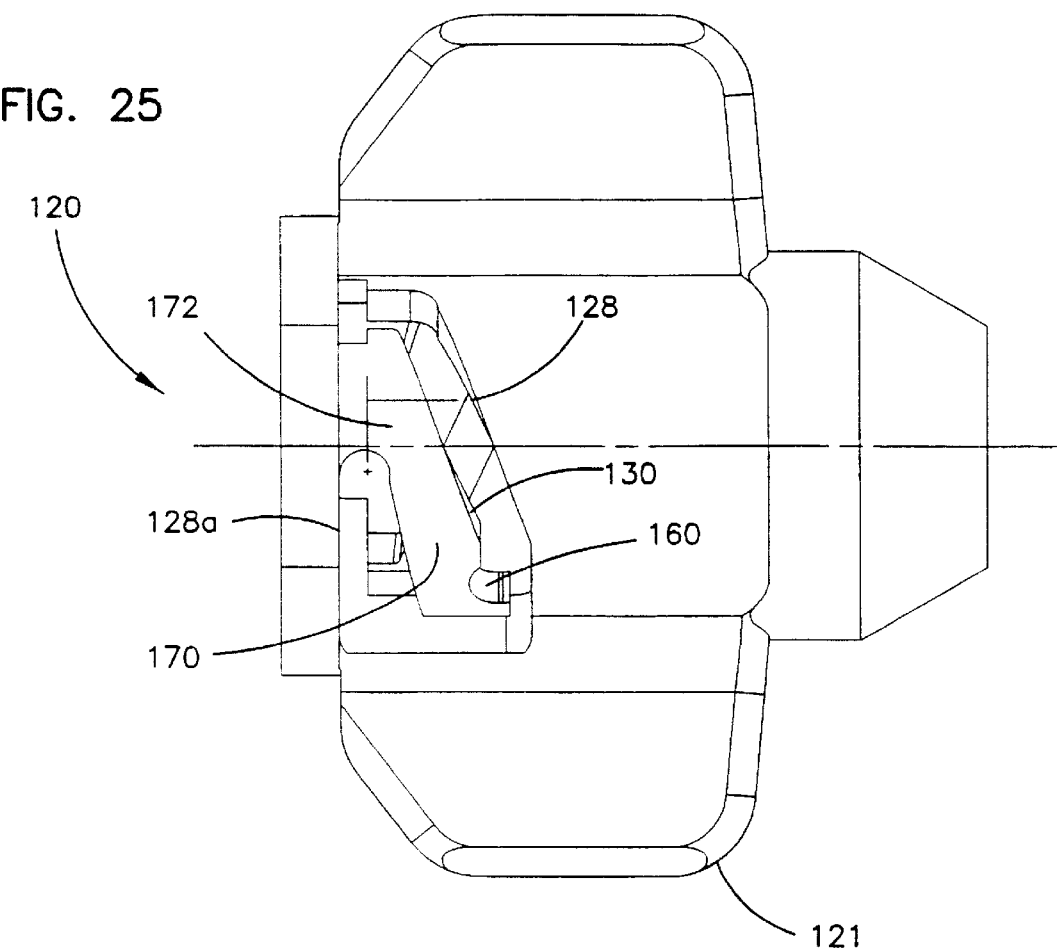
FIG. 25 is a side view of the locking sleeve.
Figure 26:
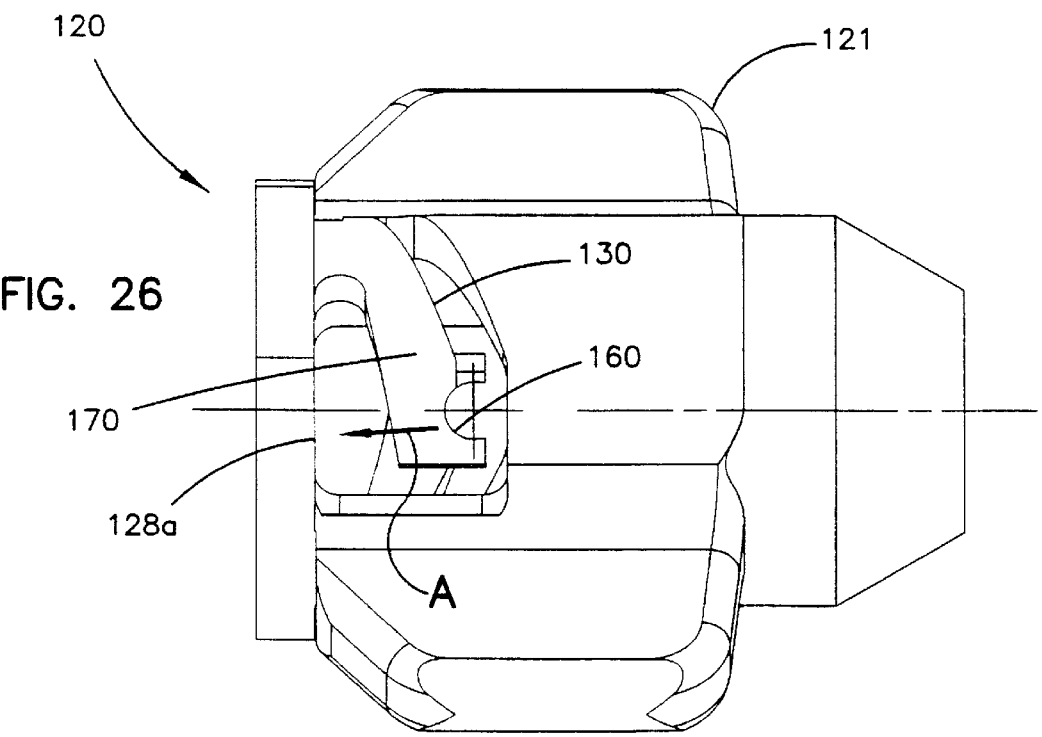
FIG. 26 is an alternative side view to FIG. 25 with the locking sleeve rotated relative to the view of FIG. 25.
Figure 27:
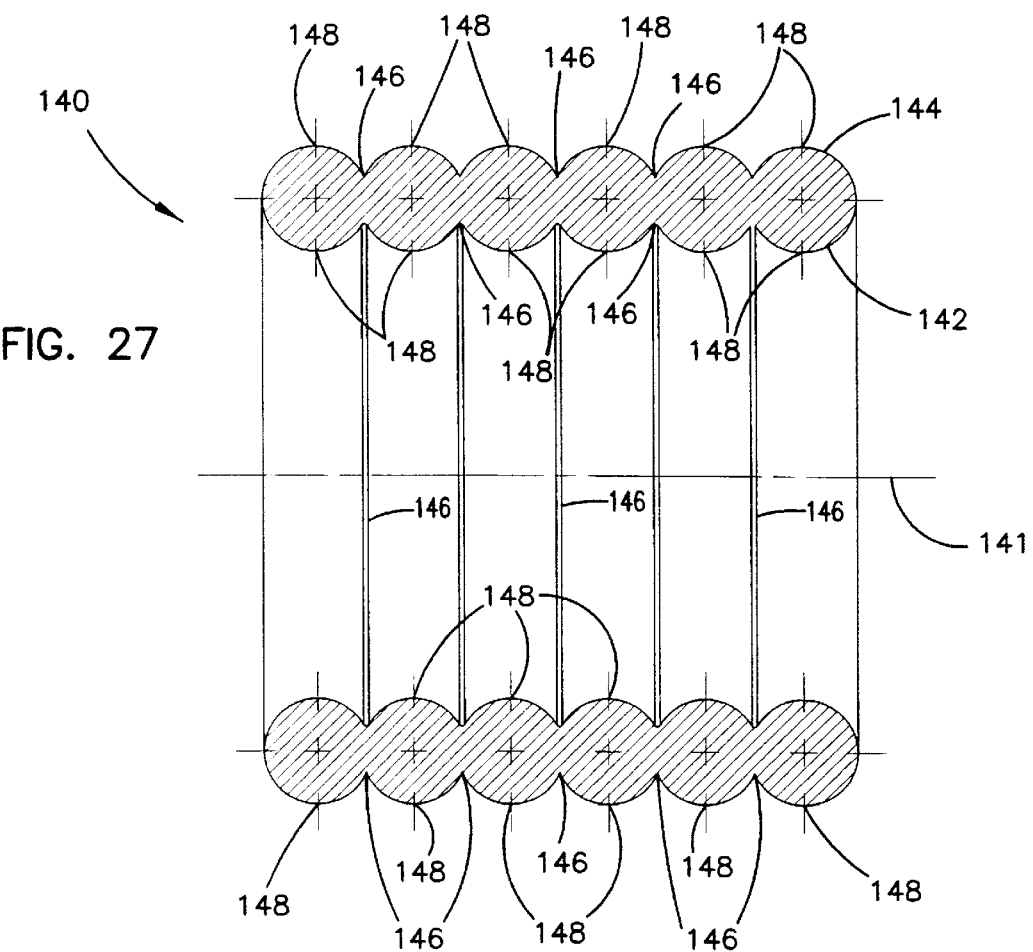
FIG. 27 is a cross-sectional side view of the compression seal.

Outlet tubes 34, 36 are shown as being made from generally tubular shaped bio-compatible metallic materials, such as titanium. Other materials, such as plastics and other non-metallic materials, in other shapes are possible. Angled shapes (FIG. 13) are provided to link two access sites to a dual lumen catheter. As will be described below, ends 68, 70 of outlet tubes 34, 36 are provided with a rounded D-shaped outer surface 69, such as shown in FIG. 14. Such shapes generally match the shapes of lumens 30, 31 of catheter 24.

Port 22 includes a body 50 and a plurality of suture holes 52 for use in suturing port 22 to the patient. Port 22 includes two pierceable septums 66 defining the two access sites 28 which close off two internal chambers 65 within body 50. Each chamber 65 is in fluid communication with one of outlet tubes 34, 36. Body 50 of port 22 can be made from a variety of materials, including all metal, all plastic, combinations thereof, or other materials which are bio-compatible. In the preferred embodiment shown, port 22 is a hybrid construction including a metallic reservoir 60, such as titanium, surrounded by an outer housing 100 made from plastic, such as polysulfone. U.S. Pat. No. 5,378,192 to SIMS Deltec of St. Paul, Minn., details various hybrid constructions for ports. The disclosure of U.S. Pat. No. 5,378,192 is hereby incorporated by reference.

Figure 8:
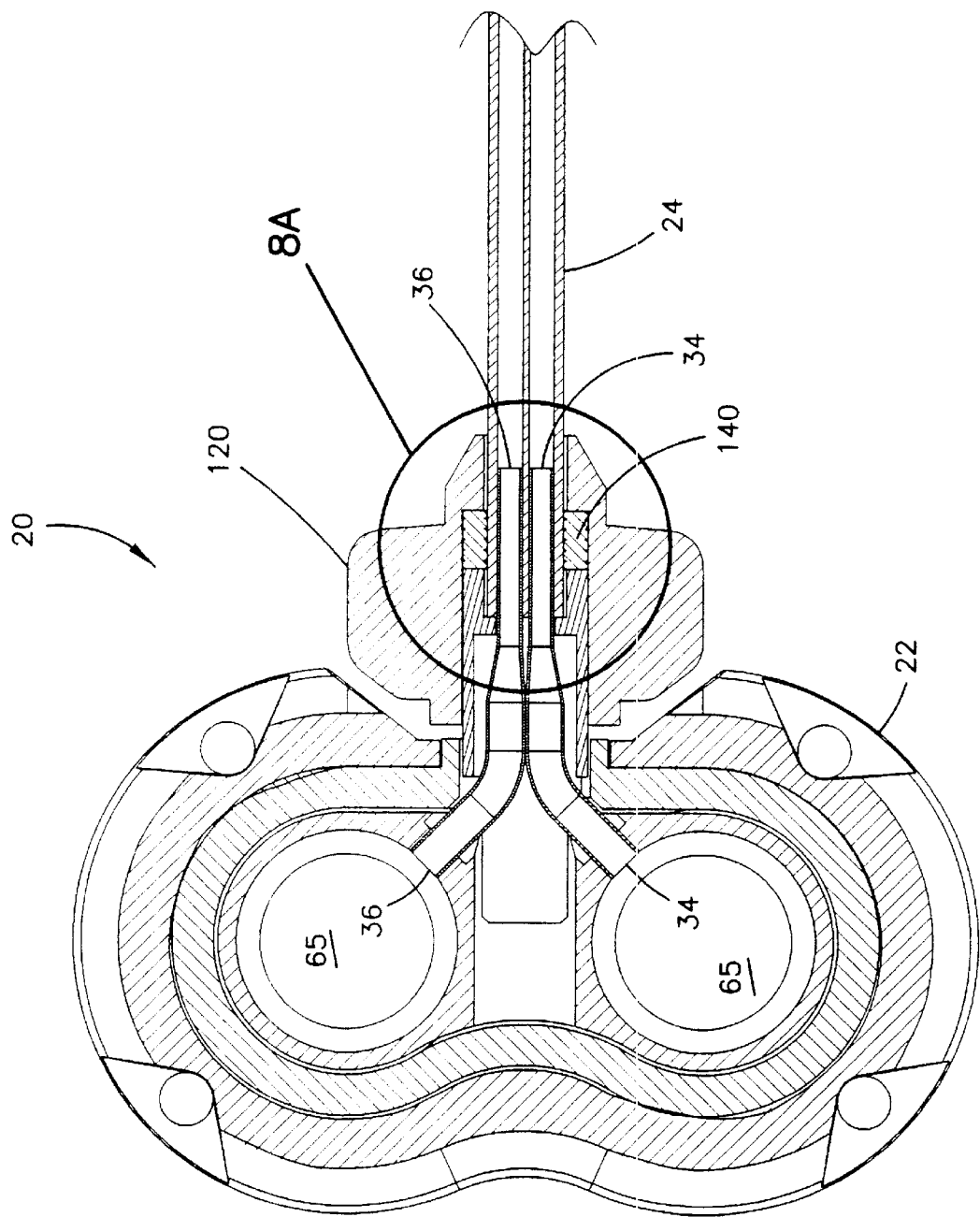
FIG. 8 is a cross-sectional top view of FIG. 7, taken along lines A—A of FIG. 4.
Figure 8A:
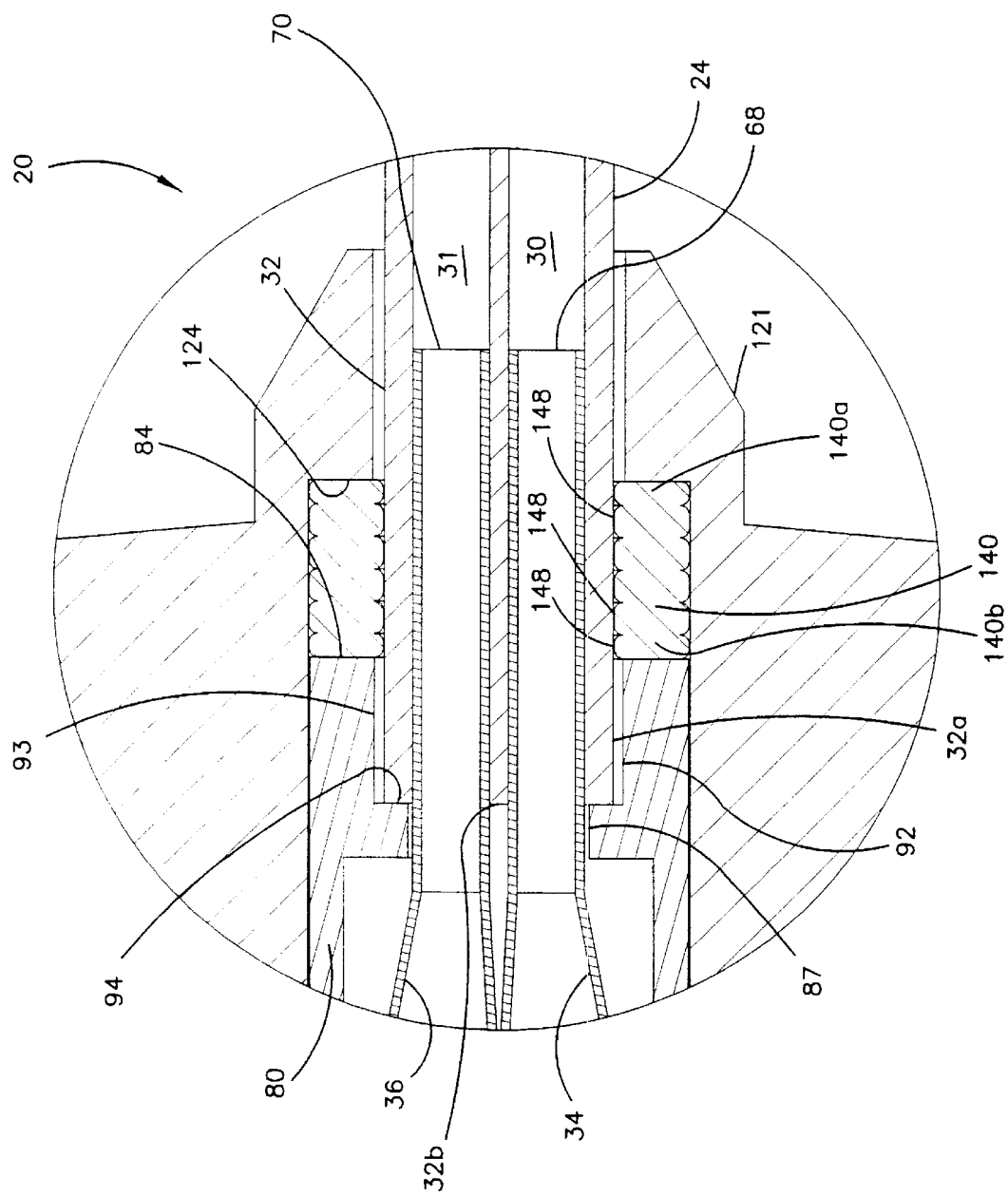
FIG. 8A is an enlarged cross-sectional top view of a portion of the portal assembly of FIG. 8 showing the catheter seal.
Figure 9:
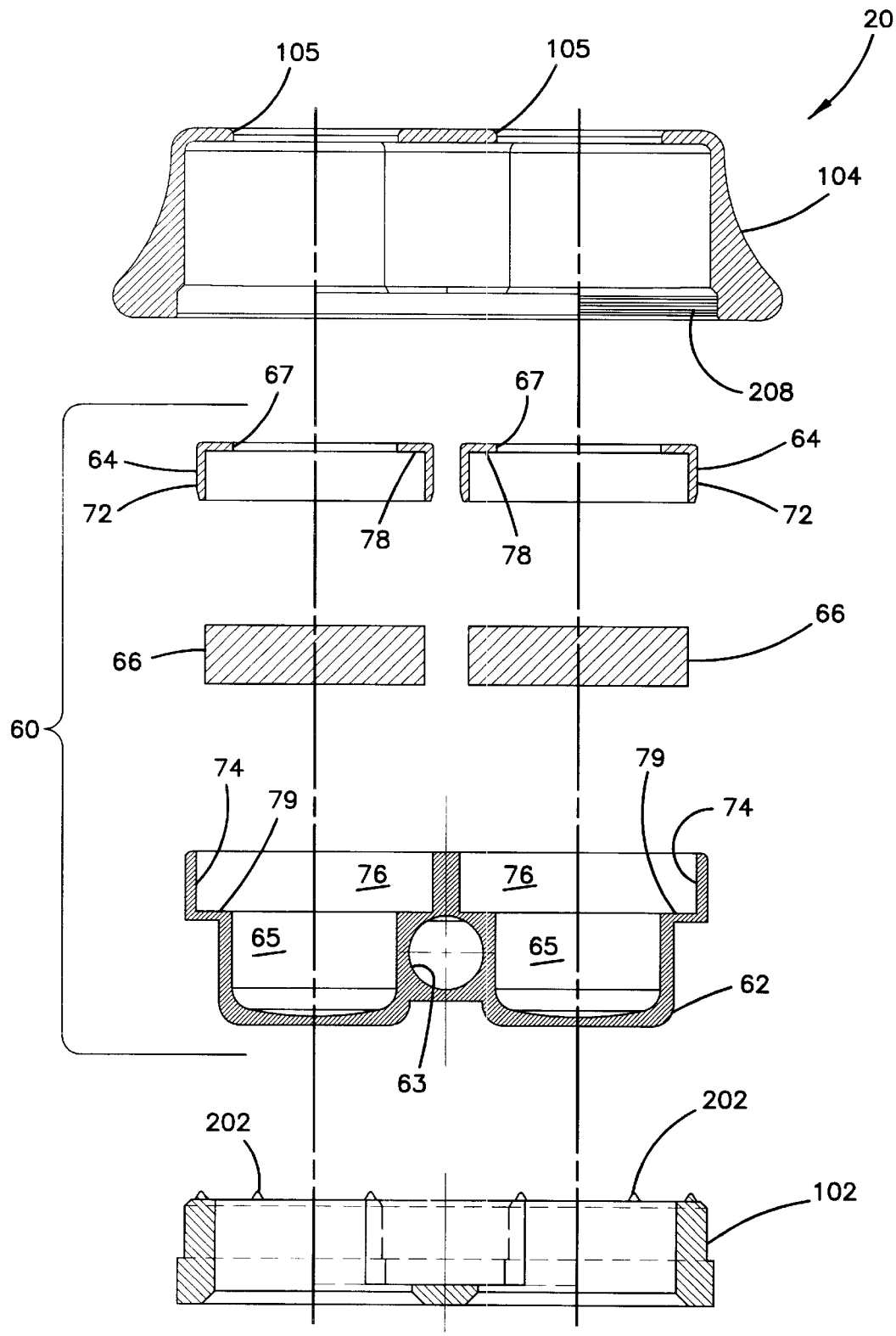
FIG. 9 is an exploded cross-sectional front view of the port before assembly, taken along lines B—B of FIG. 3, without the outlet tubes or the outlet tube support.
Figure 10:
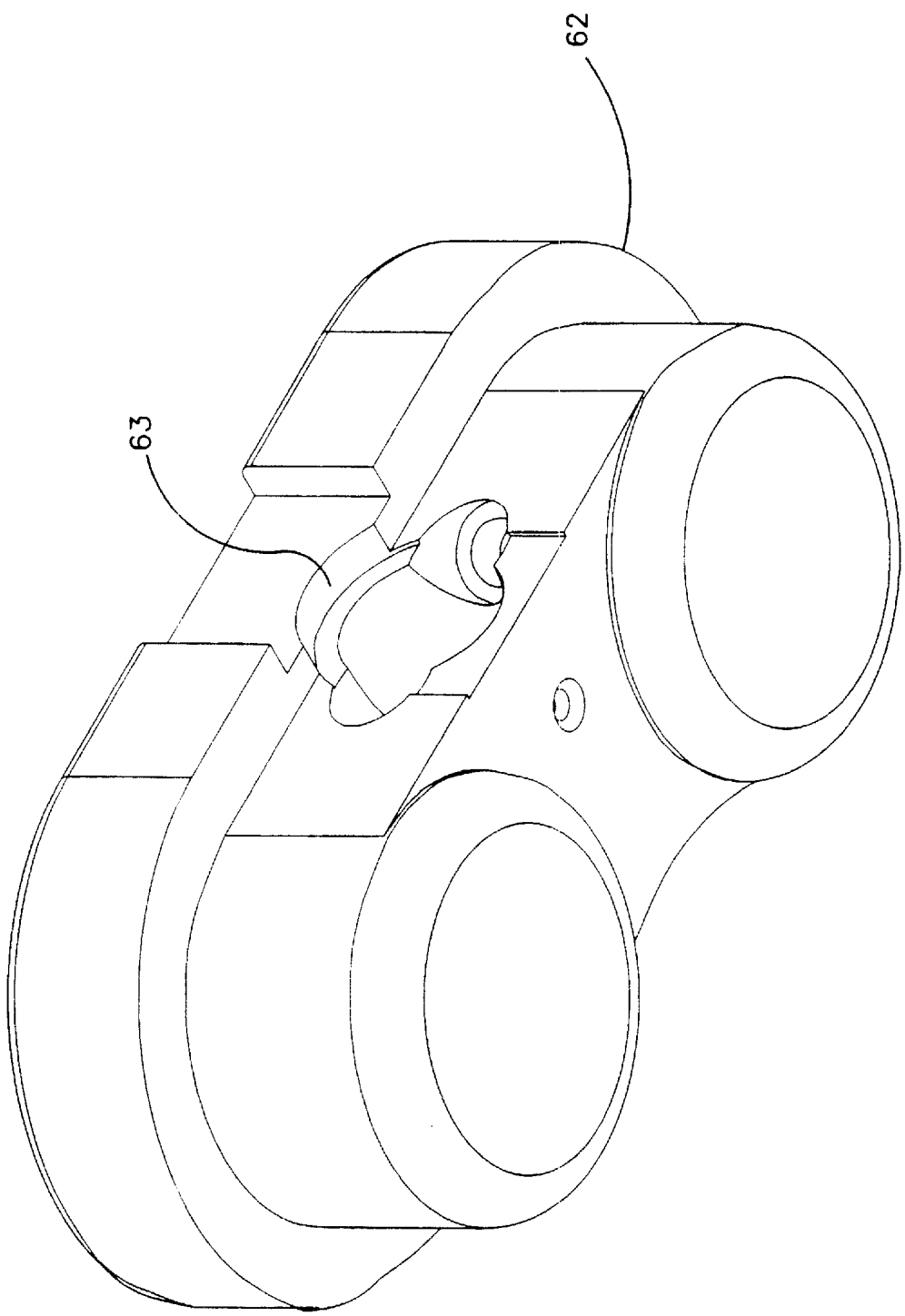
FIG. 10 is a bottom perspective view of the base of the reservoir.
Figure 11:
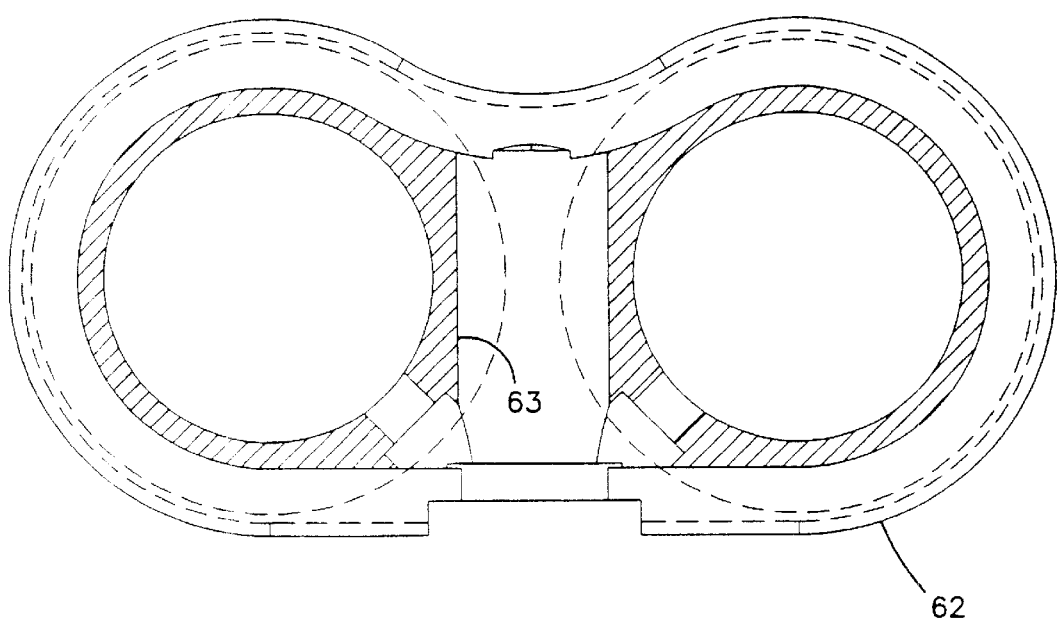
FIG. 11 is a cross-sectional top view of the base of the reservoir.
Figure 12:
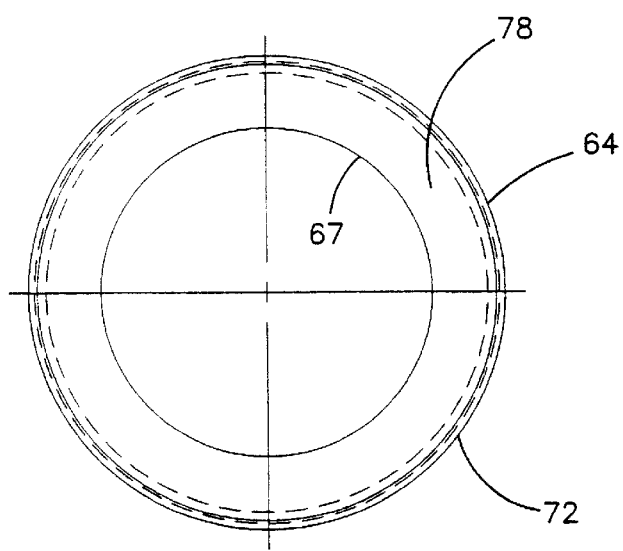
FIG. 12 is a top view of one of the caps of the reservoir.

With reference to FIGS. 9–12, reservoir 60 generally includes a base 62, and two caps 64 each with a central opening 67. Each cap 64 is interference fit to base 62. Caps 64 hold pierceable septums 66 to define enclosed chambers 65. As shown in FIG. 9, each septum 66 is wafer shaped before caps 64 compress a periphery of each septum 66 which causes the central region to bulge outward as shown in FIG. 1. An exterior surface 72 of each cap 64 engages an interior surface 74 of upper chamber 76 of base 62 to form the interference fit. Each septum 66 is trapped between a lip 78 of cap 64 and a shoulder 79 of base 62 around the periphery of septum 66. Outlet tubes 34, 36 are welded to base 62 adjacent to each chamber 65. Each of chambers 65 of reservoir 60 are in fluid communication with outlet tubes 34, 36 respectively, such as shown in FIG. 8. Therefore, fluids injected into chambers 65 via a needle which pierces one of septums 66, is in fluid communication with the respective outlet tubes 34, 36 for delivery to a site in the patient's body at distal end 25 of catheter 24.

Outer housing 100 generally includes a base 102 (FIG. 20) and a cowl 104 (FIG. 19) attached to one another around reservoir 60, such as by ultrasonic welding. Cowl 104 includes two openings 105 which expose septums 66 when housing 100 is around reservoir 60. Outlet tubes 34, 36 extend from housing 100 between a slot 106 of base 102 and a slot 108 of cowl 104. Bumps 202 on base 102 are provided for assembly tolerance compensation. During assembly, bumps 202 engage reservoir 60 and melt down to the appropriate size so as to prevent reservoir 60 from rattling within outer housing 100. Optional ridges 208 on cowl 104 (shown only on one side) are provided for extraction of the component from the injection mold.

Mounted to reservoir 60 such as by welding is a metallic support 80 (FIGS. 15–18) which supports outlet tubes 34, 36. A first end 81 of support 80 is received within a recess 63 of base 62 of reservoir 60. Support 80 is also received in slots 106, 108 of housing 100. End 81 includes two spaced apart tabs 83a, 83b. A central section 85 defines an oval shaped passage (see FIGS. 6 and 17). An inner circular shoulder 87 closely surrounds and supports outlet tubes 34, 36 (See FIGS. 8A, 17 and 18).

Now with reference to FIGS. 1, 5–8A, and 21–27, a locking sleeve 120, including an inner compression seal 140 to seal catheter 24 to outlet tubes 34, 36, mounts to support 80 to hold catheter 24 in sealing engagement with port 22. Support 80 and locking sleeve 120 form a compression fitting to seal catheter 24 to outlet tubes 34, 36. Seal 140 is concentric about a longitudinal axis 141 and defines a generally tubular shape. Seal 140 is made of resilient material, such as molded silicone. As will be described below, a preferred seal 140 includes an undulating shape. During use, seal 140 is axially compressed resulting in a radially inward acting force applied to catheter 24 to seal catheter 24 to outlet tubes 34, 36.

Support 80 extends from reservoir 60 and includes a generally circular distal end 82. Distal end surface 84 is generally perpendicular to a longitudinal axis 86 of support 80. Distal end 82 of support 80 further includes two bayonets 88, 90 on opposite sides of end 82. Support 80 further includes an inner passage 92, defining a cylindrically shaped chamber 93 at end 82 and an internal stop surface 94 for receipt of an end 32a of catheter 24. Inspection holes 180 are provided to visually inspect whether catheter 24 is positioned in chamber 93. Stop surface 94 is generally perpendicular to axis 86.

Locking sleeve 120 includes a body 121, such as made from metal (titanium), with a solid end ring 122. An inwardly projecting shoulder 124 is disposed at a second end 126 of locking sleeve 120. Inner passage 123 receives catheter 24 and seal 140, with one end 140a adjacent to shoulder 124. During use, an opposite end 140b of seal 140 is positioned adjacent to end surface 84 of support 80. Locking sleeve 120 is axially moved relative to support 80 which results in compression of seal 140. Shoulder 124 is generally perpendicular to axis 125.

Figure 7:
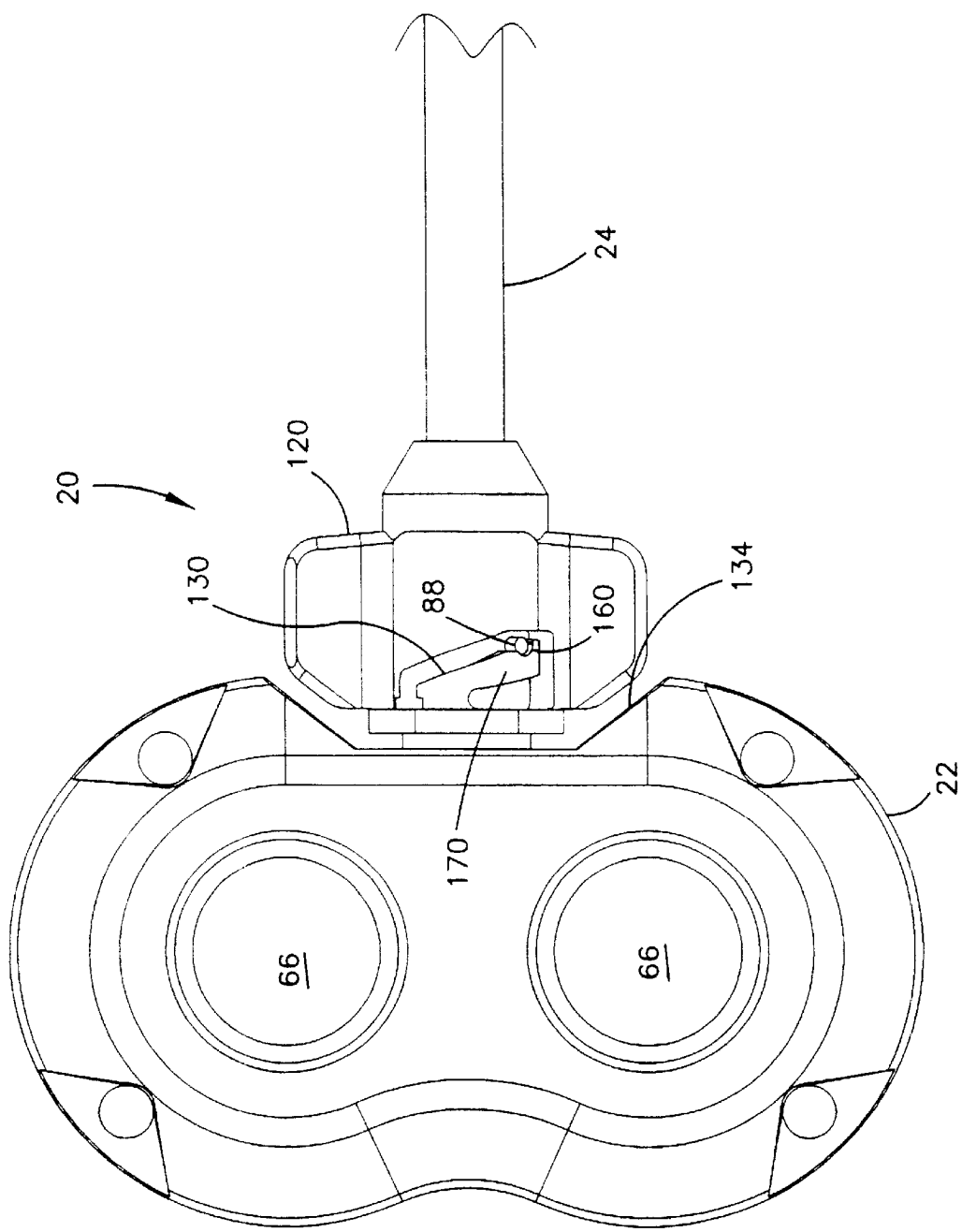
FIG. 7 is a top view of the port related to FIG. 5 showing the locking sleeve now in the locked position.

Locking sleeve 120 includes two slots 128, 129 which cooperate with bayonets 88, 90 of support 80 to mount locking sleeve 120 to support 80. Slots 128, 129 are generally identically shaped on opposite sides of locking sleeve 120. With reference to slot 128, the slot is configured as a cam surface 130 which provides camming action of locking sleeve 120 relative to support 80 for use in providing mechanical advantage to axially compress seal 140 during locking. Cam surface 130 can be angled as desired to vary the torque required to lock locking sleeve 120 and seal catheter 24. To assist in hand turning of locking sleeve 120, outwardly extending wings or lever arms 132 are provided extending from a central portion of lock ring 120. Recess 134 of port 22 is configured to fairly closely receive wings 132 of locking sleeve 120 as shown in FIG. 7. Locking sleeve 120 is shown as being turned in a clockwise direction to seal catheter 24 against outlet tubes 34, 36. A counterclockwise arrangement is also possible (not shown).

Slot 128 includes an overcenter surface or detent 160 which locates bayonet 88 to hold locking sleeve 120 in the locked position as best shown in FIGS. 1, 7, 8 and 8A. An axial force is exerted on locking sleeve 120 by seal 140 in a direction away from support 80. In the position shown, bayonet 88 cannot work its way past detent 160 and along cam surface 130 to possibly inadvertently allow catheter 24 to become separated from port 22. Also, detent 160 will not allow an errant needle to unlock locking sleeve 120. Further, the surgeon will realize instantly that connector 26 is properly locked when bayonet 88 reaches detent 160 during connection of catheter 24 to port 22. A similar detent is provided for the other bayonet 90.

Cam surface 130 is formed on a moveable lever arm 170 of locking sleeve 120 so as to provide flexibility in locking sleeve 120, to assure consistent sealing. Lever arm 170 in the preferred embodiment is formed by continuing slot 128 at 128a so as to form cam surface 130 on a projecting arm. The size and shape of connecting region 172 controls the amount of flexing allowed in arm 170. Arm 170 flexes in the direction of arrow A to assure that bayonets 88, 90 lock into detents 160. This is useful as a compensating mechanism to lessen the emphasis on the components of locking sleeve 120 having precise tolerances. With lever arm 170, a fluid tight seal is achieved over a larger range of relative sizes of body 121 and seal 140 of locking sleeve 120. Without lever arm 170, undue force may be required to reach detents 160 due to overcompression of the seal. Lever arm 170 is particularly useful in preferred connector 26 which locks through a relatively short amount of rotation (approximately 90°). Slot 128a is sized to accommodate the total range of tolerances in the components of the locking sleeve 120.

A further compensating mechanism useable in addition to, or in the alternative to, lever arm 170 is to supply flow relief areas in body 121 for excess portions of seal 140 to flow to in the compressed state while still assuring that bayonets 88, 90 reach detents 160. FIG. 29 shows a first alternative locking sleeve 120a with internal recesses or grooves 122a in body 121 a for receipt of seal 140 so as to compensate for overcompression of seal 140. FIG. 30 shows a second alternative locking sleeve 120b with holes 124b through body 121b so as to compensate for overcompression of seal 140. FIG. 31 shows a third alternative locking sleeve 120c with a flexible second end 126c. Second end 126c includes slots 128c formed in end 126c which provides flexibility in end 126c. This flexibility permits compensation for overcompression of seal 140.

Instead of flexible lever arm 170, body 121 can be provided with a spring member or an elastomer which biases cam surface 130 toward end 126 so as to allow compensation of overcompression of seal 140.

With reference to FIGS. 6, 8, 8A and 27, compression seal 140 in the preferred embodiment includes an undulating shape along an inner diameter portion 142, and also along an outer diameter portion 144. The undulating shape includes plurality of alternating rings 148 and recesses 146. Once seal 140 is compressed axially, a plurality of ring seals are formed between catheter 24 and outlet tubes 34, 36 from the inward expansion of rings 148. While the undulating shape of compression seal 140 is preferred, other shapes are possible, including generally cylindrical.

The undulating shape for seal 140 is preferred since it exerts a force in a 360° manner in a plurality of locations on catheter 24. The use of recesses 146 further assists in compensating for variations in relative sizes of the system components, while still assuring a sufficient seal is formed. Rings 148 further assist to resist pullout by catheter 24 due to the concentration of the radial forces on catheter 24 at each ring 148. The use of concentric rings 148 further provides more predictability over a cylindrical seal for the inward radial expansion of seal 140 so that a sufficient seal is formed. For example, seal 140 is less likely to produce unsymmetrical buckling than a cylindrical seal.

Rings 148 are generally circular in cross-section. It is to be appreciated that other shapes are possible with sharper or smoother curves or angles to change the nature of the ring seals on catheter 24. Also, recesses 146 can be deeper or shallower to control the compression of seal 140. Non-uniform shapes along axis 141 are possible.

Cylindrical chamber 93 within support 80 generally constrains end 32a of catheter 24 during sealing. The receipt of end 32a in chamber 93 helps to seal catheter 24. As locking sleeve 120 is locked to support 80, and seal 140 compresses catheter 24 against tubes 34, 36, catheter end 32a may flow toward stop surface 94, leading to further compression, and sealing, of catheter 24 at end 32a against stop surface 94. Also, septum 32b of catheter 32 is compressed, and further sealed, by the slight movement of outlet tubes 32, 34 toward one another from the resulting effect of radial compression by seal 140 on catheter 24.

Connector 26 generally includes the two outlet tubes 34, 36, the distal end of 82 of support 80, and locking sleeve 120. Together, outlet tubes 34, 36, and distal end 82 of support 80 form a base arrangement portion of connector 26.

Connector 26 is useable not only in portal assembly 20 but in other structures where it is desired to securably connect a device to a catheter.

A preferred use of connector 26 with catheter 24 and port 22 positions by hand the end 32 of catheter 24 over the ends 68, 70 of outlet tubes 34, 36, and end 32a within chamber 93 of end 82 of support 80 and engaged with stop surface 94. Verification that catheter 24 is properly positioned within support 80 is through inspection hole 180 (see FIG. 5). As locking sleeve 120 is rotated to mount to support 80 through bayonets 88, 90, compression seal 140 is compressed axially, which results in a radial compression on catheter 24 against outlet tubes 34, 36 to form a plurality of ring seals. Detents 160 hold bayonets 88, 90 and locking sleeve 120 in the locked state until it is desired to disconnect catheter 24 from port 22. Arm 170 pivots as needed to allow bayonets 88, 90 to reach detents 160 for locking.

Without intending to limit the invention, it is believed that connector 26, in the case of the dual outlet tube configuration, achieves its seal by seal 140 engaging catheter 24 to seal catheter 24 against outlet tubes 34, 36, and also end 32a pushed into stop surface 94 as seal 140 compresses catheter 24. Also the squeezing together of outlet tubes 34, 36 is believed to cause sealing of septum 32b of catheter 24 against tubes 34, 36.

As shown in FIGS. 14 and 28, both outlet tubes 34, 36 and lumens 30, 31 of catheter 24 include D-shapes. Such D-shapes on tubes 34, 36 include rounded corners 180. The D-shaped lumens 30, 31 include rounded corners 182. The rounded corners of the D-shapes facilitate a fluid tight seal from the compression-style fitting around a dual lumen catheter. The back-to-back D-shapes allow relatively high fluid flow in a catheter having a circular outer cross-section.

It is preferred that the D-shapes be related as follows:

> Radius of outlet tube corner–0.9×Interference ≦ Radius of lumen of catheter corner ≦ 1.05×Interference, where Interference is ≧0.

In the above noted relationship between corners, the Interference is the overall interference of the catheter internal lumen with the outlet tube outside surface.

For proper sealing, the catheter lumen inside surface needs to contact the outside surface of the outlet tube throughout the fall perimeter. Gaps may form with sharper corners when a compression-type fitting is used. When rounded corners are provided as shown in the drawings and described above, gaps are sufficiently reduced or eliminated.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A connector for a catheter comprising:
   a base arrangement including:
      two tubes extending from the base arrangement and each terminating at an end, each tube sized to be received inside the catheter;
      a surface surrounding both of the tubes positioned to engage a first end of a compression seal; and
      a bayonet extending from the base arrangement; and
   a locking sleeve engageable with the base arrangement and rotatable relative thereto, the locking sleeve including an outer body and a compression seal received within the outer body, the compression seal having first and second ends, the outer body including an inner shoulder positioned to engage the second end of the compression seal, the outer body including a cam slot for receiving the bayonet, the cam slot including an angled portion, the cam slot including an overcenter portion, the locking sleeve including a compensating mechanism for allowing further rotation of the locking sleeve at an over compression condition of the compression seal, the compression seal engageable with the catheter to seal the catheter to the tubes when the locking sleeve is mounted to the base arrangement.

2. The connector of claim 1, wherein a portion of the cam slot is defined by a movable lever arm of the outer body, the moveable lever arm forming at least a portion of the compensating mechanism.

3. The connector of claim 1, wherein the compression seal includes an undulating configuration in an uncompressed state, wherein the compression seal has an inner surface and an outer surface each defining an undulating shape.

4. The connector of claim 1, wherein the base arrangement defines a catheter tip recess having a generally cylindrical inner surface, and a stop surface, the catheter tip surrounded by the inner surface, and the tip engageable with the stop surface.

5. The connector of claim 4, wherein the base arrangement defines an inspection hole communicating with the catheter tip recess to allow viewing of the catheter tip positioned in the catheter tip recess before the locking sleeve is mounted to the base arrangement.

6. The connector of claim 1, wherein the base arrangement forms a portion of an implantable port including a resealable septum.

7. The connector of claim 1, wherein the base arrangement includes two bayonets, and wherein the locking sleeve includes two cam slots, each cam slot defined by a moveable lever arm.

8. The connector of claim 1, wherein the tubes define back-to-back general D shapes.

9. A connector for a dual lumen catheter comprising:
   a) a base arrangement including:
      1) two tubes extending from the base arrangement and each terminating at an end, each tube sized to be received inside the catheter, each end defining a general D shape, each D shape facing back-to-back with the other D shape, each D shape having rounded corners;
      2) a surface surrounding both of the tubes positioned to engage a first end of a compression seal;
      3) a bayonet extending from the base arrangement;
      4) the base arrangement defining a catheter tip recess having a generally cylindrical inner surface, and a stop surface positioned adjacent to the outlet tubes;
   b) a locking member mountable to the base arrangement and rotatable relative thereto, the locking member including a surface to engage a second end of a compression seal, the locking member including a cam slot for receiving the bayonet, the cam slot including an angled portion, the cam slot including an overcenter portion;
   c) a compression seal positioned between the surface of the base arrangement and the surface of the locking member, the compression seal having first and second ends, the compression seal including an undulating configuration in an uncompressed state, wherein the compression seal has an inner surface and an outer surface each defining an undulating shape, the compression seal engageable with the catheter to seal the catheter to the tubes when the locking member is mounted to the base arrangement, the catheter tip surrounded by the inner surface and engageable with the stop surface; and
   d) a compensating mechanism for allowing further rotation of the locking member at an overcompression condition of the compression seal.

10. A method of using a catheter connector, comprising the steps of:
    providing a base arrangement of the connector including a tube and a bayonet;
    positioning a catheter on the tube;
    providing a locking sleeve lockable to the base arrangement, the locking sleeve including a compression seal compressible between the locking sleeve and the base arrangement, the locking ring including a cam slot on a lever arm, the cam slot including a detent;
    engaging the cam slot with the bayonet;
    compressing the seal between the locking sleeve and the base arrangement; and
    moving the lever arm as the bayonet is moved along the cam slot to the detent.

11. The method of claim 10, wherein the base arrangement includes two tubes, each having a general D shape.

* * * * *